United States Patent
Hu et al.

(10) Patent No.: US 10,633,363 B2
(45) Date of Patent: Apr. 28, 2020

(54) EPAC1 ACTIVATORS AS HIV LATENCY REVERSAL AGENTS (LRA)

(71) Applicants: Haitao Hu, Galveston, TX (US); Jia Zhou, Galveston, TX (US); Zhiqing Liu, Galveston, TX (US); Xiuzhen Fan, Galveston, TX (US)

(72) Inventors: Haitao Hu, Galveston, TX (US); Jia Zhou, Galveston, TX (US); Zhiqing Liu, Galveston, TX (US); Xiuzhen Fan, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 0 days.

(21) Appl. No.: 16/034,558

(22) Filed: Jul. 13, 2018

(65) Prior Publication Data

US 2019/0092749 A1 Mar. 28, 2019

Related U.S. Application Data

(60) Provisional application No. 62/532,545, filed on Jul. 14, 2017.

(51) Int. Cl.
| | | |
|---|---|---|
| C07D 401/12 | (2006.01) | |
| C07D 307/79 | (2006.01) | |
| C07D 209/12 | (2006.01) | |
| C07D 209/24 | (2006.01) | |
| C07D 417/12 | (2006.01) | |
| A61P 31/18 | (2006.01) | |

(52) U.S. Cl.
CPC ............ *C07D 401/12* (2013.01); *A61P 31/18* (2018.01); *C07D 209/12* (2013.01); *C07D 209/24* (2013.01); *C07D 307/79* (2013.01); *C07D 417/12* (2013.01)

(58) Field of Classification Search
CPC .. C07D 401/12; C07D 417/12; C07D 209/24; C07D 307/79; C07D 209/12; A61P 31/18
See application file for complete search history.

(56) References Cited

U.S. PATENT DOCUMENTS 9,539,256 B2  1/2017  Cheng et al.

FOREIGN PATENT DOCUMENTS

WO  WO-2018183626 A1 * 10/2018 ............ A61K 45/06

OTHER PUBLICATIONS

Ye, N., "Identification of novel 2-(benzo [d] isoxazol-3-yl)-2-oxo-N-phenylacetohydrazonoyl cyanide analoguesas potent epac antagonists." European journal of medicinal chemistry 134 (2017): 62-71.*

Fouda, A. S., "Some Schiff base compounds as inhibitors for corrosion of carbon steel in acidic media." Protection of Metals and Physical Chemistry of Surfaces 48.4 (2012): 477-486.*

Behbehani, H., "Studies with 3-Oxoalkanonitriles: Synthesis and Reactivity of 3-Oxo-3-(1-methylindoloyl) propanenitrile." Heterocycles 78.12 (2009): 3081-3090.*

Aflaki M, et al. (2014) Exchange protein directly activated by cAMP mediates slow delayed-rectifier current remodeling by sustained beta-adrenergic activation in guinea pig hearts. Circ Res 114(6):993-1003.

Agosto LM, et al. (2007) HIV-1 integrates into resting CD4+ T cells even at low inoculums as demonstrated with an improved assay for HIV-1 integration. Virology 368(1):60-72.

Almahariq M, et al. (2013) A novel EPAC-specific inhibitor suppresses pancreatic cancer cell migration and invasion, Mol Pharmacol 83(1):122-128.

Almahariq M, et al, (2015) Exchange protein directly activated by cAMP modulates regulatory T-cell-mediated immunosuppression. Biochem J 465(2):295-303.

Archin NM & Margolis DM (2014) Emerging strategies to deplete the HIV reservoir. Curr Opin Infect Dis 27(1):29-35.

Archin NM, et al. (2009) Expression of latent HIV induced by the potent HDAC inhibitor suberoylanilide hydroxarnic acid. AIDS Res Hum Retroviruses 25(2):207-212.

Archin NM, et al. (2012) Administration of vorinostat disrupts HIV-1 latency in patients on antiretroviral therapy. Nature 487(7408):482-485.

Baljinnyam E, et al. (2010) Exchange protein directly activated by cyclic AMP increases melanoma cell migration by a Ca2+-dependent mechanism. Cancer Res 70(13):5607-5617.

Beavo JA & Brunton LL (2002) Cyclic nucleotide research—still expanding after half a century. Nat Rev Mol Cell Biol 3(9):710-718.

(Continued)

*Primary Examiner* — John M Mauro
(74) *Attorney, Agent, or Firm* — Hylton-Rodic Law PLLC

(57) ABSTRACT

The invention relates generally to novel EPAC1 activators, such as Formula I and the preparation thereof as well as the use of EPAC1 activators as human immunodeficiency virus (HIV) latency reversal agents (LRAs).

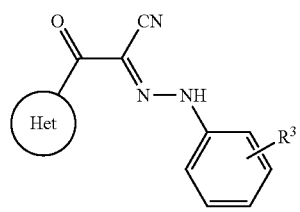

Formula I

10 Claims, 26 Drawing Sheets

(9 of 26 Drawing Sheet(s) Filed in Color)

(56) References Cited

OTHER PUBLICATIONS

Blazkova J, et al. (2012) Effect of histone deacetylase inhibitors on HIV production in latently infected, resting CD4(+) T cells from infected individuals receiving effective antiretroviral therapy. J Infect Dis 206(5):765-769.

Booiman T, Loukachov VV, van Dort KA, van 't Wout AB, & Kootstra NA (2015) DYRK1A Controls HIV-1 Replication at a Transcriptional Level in an NFAT Dependent Manner, PLoS One 10(12):e0144229.

Brandt B, Abou-Eladab EF, Tiedge M, & Walzel H (2010) Role of the JNK/c-Jun/AP-1 signaiing pathway in galectin-1- induced T-cell death. Cell Death Dis 1:e23.

Brennesvik EO, et al. (2005) Adrenaline potentiates insulin-stimulated PKB activation via cAMP and Epac: implications for cross talk between insulin and adrenaline. Cell Signal 17(12):1551-1559.

Bryce PJ, Dascombe MJ, & Hutchinson IV (1999) Immunomodulatory effects of pharmacological elevation of cyclic AMP in T lymphocytes proceed via a protein kinase a independent mechanism. Immunopharmacology 41(2):139-146.

Bullen CK, Laird GM, Durand CM, Siliciano JD, & Siliciano RF (2014) New ex vivo approaches distinguish effective and ineffective singe agents for reversing HIV-1 latency in vivo. Nat Med 20(4):425-429.

Cary DC & Peterlin BM (2016) Targeting the latent reservoir to achieve functional HIV cure. F1000Res 5.

Chen H, et al. (2012) 5-Cyano-6-oxo-1,6-dihydro-pyrimidines as potent antagonists targeting exchange proteins directly activated by cAMP. Bioorganic & medicinal chemistry letters 22(12):4038-4043.

Chen H, et al. (2013) A combined bioinforrnatics and chemoinformatics approach for developing asymmetric bivalent AMPA receptor positive allosteric modulators as neuroprotective agents. ChemMedChem 8(2):226-230.

Chen H, et al. (2013) Efficient Synthesis of ESI-09, A Novel Non-cyclic Nucleotide EPAC Antagonist. Tetrahedron Lett 54(12):1546-1549.

Chen H. et al. (2013) Fragment-based drug design and identification of HJC0123, a novel orally bioavailabe STAT3 inhibitor for cancer therapy. European journal of medicinal chemistry 62:498-507.

Chen H, et al. (2014) Discovery of potent anticancer agent HJC0416, an orally bioavailable small molecule inhibitor of signal transducer and activator of transcription 3 (STAT3). Eur J Med Chem 82:195-203.

Chen H, et al. (2014) Recent advances in the discovery of small molecules targeting exchange proteins directly activated by cAMP (EPAC). J Med Chem 57(9):3651-3665.

Chen H, et al. (2015) Evolutions in fragment-based drug design: the deconstruction-reconstruction approach. Drug discovery today 20(1):105-113.

Chen H, et al. (2016) Mechanosensing by the alpha6-integrin confers an invasive fibroblast phenotype and mediates lung fibrosis. Nat Commun 7:12564.

Cheng X, Ji Z, Tsalkova T, & Mei F (2008) Epac and PKA: a tale of two intracellular cAMP receptors, Acta Biochim Biophys Sin (Shanghai) 40(7):651-662.

Chugh P, et al. (2008) Akt inhibitors as an HIV-1 infected macrophage-specific anti-viral therapy. Retrovirology 5:11. I 1.

Chun TW, Moir S, & Fauci AS (2015) HIV reservoirs as obstacles and opportunities for an HIV cure. Nat Immunol 166):584-589.

Contreras X, et al. (2009) Suberoylanilide hydroxamic acid reactivates HIV from latently infected cells. J Biol Chem 284 (11):6762-6769.

Dahabieh MS, Battivelli E, & Verdin E (2015) Understanding HIV latency: the road to an HIV cure. Annu Rev Med 66:407-421.

de Rooij J, et al, (1998) Epac is a Rap1 guanine-nucleotide-exchange factor directly activated by cyclic AMP. Nature 396(6710):474-477.

Decks SG (2012) HIV: Shock arid kill. Nature 487(7408):439-440.

Diaz L, et al. (2015) Bryostatin activates HIV-1 latent expression in human astrocytes through a PKC and NF-kB-dependent mechanism, Sci Rep 5:12442.

Donahue DA, et al. (2013) Cellular and molecular mechanisms involved in the establishment of HIV-1 latency.

Fernando K, Hu H, Ni H, Hoxie JA, & Weissman D (2007) Vaccine-delivered Hiv envelope inhibits CD4(+) T-cell activation, a mechanism for poor HIV vaccine responses. Blood 109(6):2538-2544.

Gelman BB, et al. (2012) The National NeuroAIDS Tissue Consortium brain gene array: two types of HIV-associated neurocognitive impairment. PLoS One 7(9):e46178.

Gong B, et al. (2013) Exchange protein directly activated by cAMP plays a critical role in bacterial invasion during fatal rickettsioses. Proc Natl Acad Sci U S A 110(48).19615-19620.

Grandoch M, Roscioni SS, & Schmidt M (2010) The role of Epac proteins, novel cAMP mediators, in the regulation of immune, lung and neuronal function. Br J Pharmacol 159(2):265-284.

Gu Y, Wang C, Li G, & Huang LY (2016) Express: F-actin links Epac-PKC signaling to purinergic P2X3 receptors sensitization in dorsal root ganglia following inflammation. Mol Pain 12.

Han B, et al. (2015) Small-Molecule Bcl2 BH4 Antagonist for Lung Cancer Therapy. Cancer Cell 27(6):852-863.

Heaton RK, et al, (2015) Neurocognitive change in the era of HIV combination antiretroviral therapy: the longitudinal Charter study. Clin Infect Dis 60(3):473-480.

Hohne K, et al. (2016) Virion encapsidated HIV-1 Vpr induces NFAT to prime non-activated T cells for productive infection. Open Biol 6(7).

Hu H, et al. (2011) SIV antigen immunization induces transient antigen-specific T cell responses and selectively activates viral replication in draining lymph nodes in retroviral suppressed rhesus macaques. Retrovirology 8:57.

Hu H, et al. (2013) Distinct gene-expression profiles associated with the susceptibility of pathogen-specific CD4 T cells to HIV-1 infection. Blood 121(7):1136-1144.

Hu H, et al. (2014) Preferential infection of human Ads-specific CD4 T cells by HIV in Ad5 naturally exposed and recombinant Ad5-HIV vaccinated individuals. Proc Natl Acad Sci U S A 111(37):13439-13444.

Hu H, Fernando K, Ni H, & Weissman D (2008) HIV envelope suppresses CD4+ T cell activation independent of T regulatory cells. J Immunol 180(8):5593-5600.

International ASSWGoHIVC, et al. (2012) Towards an HIV cure: a global scientific strategy. Nat Rev Immunol 12 (8):607-614.

Jiang G, et al. (2015) Synergistic Reactivation of Latent HIV Expression by Ingenol-3-Angelate, PEP005, Targeted NF-kB Signaling in Combination with JQ1 Induced p-TEFb Activation. PLoS Pathog 11(7):e1005066.

Kawasaki H, et al. (1998) A family of cAMP-binding proteins that directly activate Rap1. Science 282(5397):2275-2279.

Khan SZ, Hand N, & Zeichner SL (2015) Apoptosis-induced activation of HIV-1 in latently infected cell lines. Retrovirology 12:42.

Korin YD, Brooks DG, Brown S, Korotzer A, & Zack JA (2002) Effects of prostratin on T-cell activation and human immunodeficiency virus latency. J Virol 76(16):8118-8123.

Kumar A, Darcis G, Van Lint C, & Herbein G (2015) Epigenetic control of HIV-1 post integration latency: implications for therapy. Clin Epigenetics 7:103.

Laird GM, et al. (2013) Rapid quantification of the latent reservoir for HIV-1 using a viral outgrowth assay. PLoS Pathog 9(5):e1003398.

Lipinski CA, Lombardo F, Dominy BW, & Feeney PJ (2001) Experimental and computational approaches to estimate solubility and permeability in drug discovery and development settings. Advanced drug delivery reviews 46(1-3):3-26.

Liu F, et al. (2016) Sequential Dysfunction and Progressive Depletion of Candida albicans-Specific CD4 T Cell Response in HIV-1 Infection. PLoS Pathog 12(6):e1005663.

Liu Z, et al, (2016) Direct Activation of Bax Protein for Cancer Therapy. Med Res Rev 36(2):313-341.

(56) References Cited

OTHER PUBLICATIONS

Lohse N, et al. (2007) Survival of persons with and without HIV infection in Denmark, 1995-2005. Ann Intern Med 146 (2):87-95.
Mandal M, et al. (2005) The Akt inhibitor KP372-1 suppresses Akt activity and cell proliferation and induces apoptosis in thyroid cancer cells. Br J Cancer 92(10):1899-1905.
Clemente, MI et al. (2014) Prostaglandin E2 Reduces the Release and Infectivity of New Cell-Free Virions and Cell-To-Cell HIV-1 Transfer, PLoS One 9(2): e85230.
marin B, et al. (2009) Non-AIDS-defining deaths and immunodeficiency in the era of combination antiretroviral therapy. AIDS 23(13):1743-1753.
Matalon S, et al. (2010) the historic deacetylase inhibitor ITF2357 decreases surface CXCR4 and CCR5 expression on CD4(+) T-cells and monocytes and is superior to valproic acid for latent HIV-1 expression in vitro. J Acquir Immune Defic Syndr 54(1):1-9.
McCoy LE, et al, (2014) Neutralisation of HIV-1 cell-cell spread by human and llama antibodies. Retrovirology 11:83.
McDonough KA & Rodriguez A (2011) The myriad roles of cyclic AMP in microbial pathogens: from signal to sword. Nat Rev Microbiol 10(1):27-38.
Mei FC, et al. (2002) Differential signaling of cyclic AMP: opposing effects of exchange protein directly activated by cyclic AMP and cAMP-dependent protein kinase on protein kinase B activation, J Biol Chem 277(13):11497-11504.
Meyer-Baese A, Wildberger J, Meyer-Baese U, & Nilsson CL (2014) Data analysis techniques in phosphoproteomics. Electrophoresis 35(24):3452-3462.
Mori N, et al. (2002) Bay 11-7082 inhibits transcription .factor Nf-kappaB arid induces apoptosis of HTLV-I-infected T-cell lines and primary adult T-cell leukemia cells. Blood 100(5):1828-1834. I.
Mosenden R & Taskeri K (2011) Cyclic AMP-mediated immune regulation—overview of mechanisms of action in T cells. Cell Signal 23(6):1009-1016.
Nicholas D, et al. (2015) Quantitative proteomics reveals a role for epigenetic reprogramming during human monocyte differentiation. Mol Cell Proteomics 14(1):15-29.
Nijholt Im, et al. (2008) Neuronal AKAP150 coordinates PKA and Epac-mediated PKB/Akt phosphorylation, Cell Signal 20(10):1715-1724.
Nilsson CL (2012) Advances in quantitative phosphoproteomics. Anal Chem 84(2):735-746.
Nilsson CL, et al. (2010) Quantitative phosphoproteomic analysis of the STAT3/IL-6/HIF1alpha signaling network: an initial study in GSC11 glioblastoma stem cells. J Proteome Res 9(1):430-443.
Parnell E, Palmer TM, & Yarwood SJ (2015) The future of EPAC-targeted therapies: agonism versus antagonism. Trends Pharmacol Sci 36(4):203-214.
Perez M, et al, (2010) Bryostatin-1 synergizes with histone deacetylase inhibitors to reactivate HIV-1 from latency. Curr HIV Res 8(6):418-429.
Pires DE, Blundell TL, & Ascher DB (2015) pkCSM: Predicting Small-Molecule Pharmacokinetic and Toxicity Properties Using Graph-Based Signatures. J Med Chem 58(9):4066-4072.
Quivy V, et al. (2002) Synergistic activation of human immunodeficiency virus type 1 promoter activity by NF-kappaB arid inhibitors of deacetylases: potential perspectives for the development of therapeutic strategies. J Virol 76 (21):11091-11103.
Reber L, Vermeulen L, Haegeman G, & Frossard N (2009) Ser276 phosphorylation of NF-kB p65 by MSK1 controls SCF expression in inflammation. PLoS One 4(2):e4393.
Reuse S, et al. (2009) Synergistic activation of HIV-1 expression by deacetylase inhibitors arid prostratin: implications for treatment of latent infection. PLoS One 4(6):e6093.
Roehrl MH, et al. (2004) Selective inhibition of caicineurin-NFAT signaling by blocking protein-protein interaction with small organic molecules. Proc Natl Acad Sci U S A 101(20):7554-7559.
Ruelas DS & Greene WC (2013) an integrated overview of HIV-1 latency. Cell 155(3):519-529.
Sahu GK & Cloyd MW (2011) Latent HIV in primary T lymphocytes is unresponsive to histone deacetylase inhibitors. Virol J 8:400.
Schmidt M, Dekker FJ, & Maarsingh H (2013) Exchange protein directly activated by cAMP (epac): a multidomain cAMP mediator in the regulation of diverse biological functions. Pharmacol Rev 65(2):670-709.
Schmidt T, Schrnid-Burgk JL, Ebert TS, Gaidt MM, & Hornung V (2016) Designer Nuclease-Mediated Generation of Knockout THP1 Cells. Methods Mol Biol 1338:261-272.
Schuetz A, et al. (2014) Initiation of ART during early acute HIV infection preserves mucosal Th17 function and reverses HIV-related immune activation. PLoS Pathog 10(12):e1004543.
Sedaghat AR, Siliciano RF, & Wilke CO (2008) Low-level HIV-1 replication and the dynamics of the resting CD4+ T cell reservoir for HIV-1 in the setting of HAART. BMC Infect Dis 8:2.
Sharma S, et al. (2011) Dephosphorylation of the nuclear factor of activated T cells (NFAT) transcription factor is regulated by an RNA-protein scaffold complex. Proc Natl Acad Sci U S A 108(28):11381-11386.
Shirshev SV (2011) Role of Epac proteins in mechanisms of cAMP-dependent immunoregulation. Biochemistry (Mosc) 76(9):981-998.
Siliciano JD, et al. (2016) Recent developments in the effort to cure HIV infection: going beyond N = 1, J Clin Invest.;126:409-414.
Siliciano RF & Greene WC (2011) HIV latency. Cold Spring Harb Perspect Med 1(1):a007096.
Spina CA, et al. (2013) An in-depth comparison of latent HIV-1 reactivation in multiple cell model systems and resting CD4+ T cells from aviremic patients. PLoS Pathog 9(12):e1003834.
Stokman G, et al. (2011) Epac-Rap signaling reduces cellular stress and ischemia-induced kidney failure. J Am Soc Nephrol 22(5):859-872.
Tao X, et al. (2014) Blocking of exchange proteins directly activated by cAMP leads to reduced replication of Middle East respiratory syndrome coronavirus. J Virol 88(7):3902-3910.
Tetko IV (2005) Computing chemistry on the web. Drug discovery today 10(22):1497-1500.
Tetko IV, et al. (2005) Virtual computational chemistry laboratory—design and description. Journal of computer-aided molecular design 19(6):453-463.
Tripathy MK, Abbas W, & Herbein G (2011) Epigenetic regulation of HIV-1 transcription. Epigenomics 3(4):487-502.
Van Lint C, Bouchat S, & Marcello A (2013) HIV-1 transcription and latency: an update. Retrovirology 10:67.
Vliern MJ, et al. (2008) 8-pCPT-2'-O-Me-cAMP-AM: an improved Epac-selective cAMP analogue. Chembiochem 9 (13):2052-2054.
Vouillot L, Thelie A, & Pollet N (2015) Comparison of T7E1 and surveyor mismatch cleavage assays to detect mutations triggered by engineered nucleases, G3 (Bethesda) 5(3):407-415.
Wang Y, et al. (2017) Suppression of the Growth and invasion of Human Head and Neck Squamous Cell Carcinomas via Regulating STAT3 Signaling and miR-21/beta-catenin Axis with HJC0152, Mol Cancer Ther.
Wild CT, et al. (2016) Functionalized N,N-Diphenylarnines as Potent and Selective EPAC2 Inhibitors. ACS Med Chem Lett 7(5):460-464.
Xing S, et al. (2011) Disuifirarn reactivates latent HIV-1 in a Bcl-2-transduced primary CD4+ T cell model without inducing global T cell activation. J Virol 85(12):6060-6064.
Yan K, Gao LN, Cui YL, Zhang Y, & Zhou X (2016) The cyclic AMP signaling pathway: Exploring targets for successful drug discovery (Review). Mol Med Rep 13(5):3715-3723.
Ye N & Zhou J (2014) KRAS—An Evolving Cancer Target, Austin J Cancer Clin Res 1(1).
Ye N, Ding Y, Wild C, Shen Q, & Zhou J (2014) Small molecule inhibitors targeting activator protein 1 (AP-1). J Med Chem 57(16):6930-6948.
Ye N, et al. (2015) Structure-Activity Relationship Studies of Substituted 2-(Isoxazol-3-yl)-2-oxo-N'-phenyl- Cyanide Analogues: Identification of Potent Exchange Proteins Directly Activated by cAMP (EPAC) Antagonists. J Med Chem 58(15):6033-6047.

(56) References Cited

OTHER PUBLICATIONS

Ye N, et al. (2017) Identification of novel 2-(benzo[d]isoxazoi-3-yl)-2-oxo-Nphenylacetohydrazonoyl cyanide analogues as potent EPAC antagonists.

Zhu Y, et al. (2015) Biochemical and pharmacological characterizations of ESI-09 based EPAC inhibitors: defining the ESI-09 "therapeutic window". Sci Rep 5:9344.

* cited by examiner

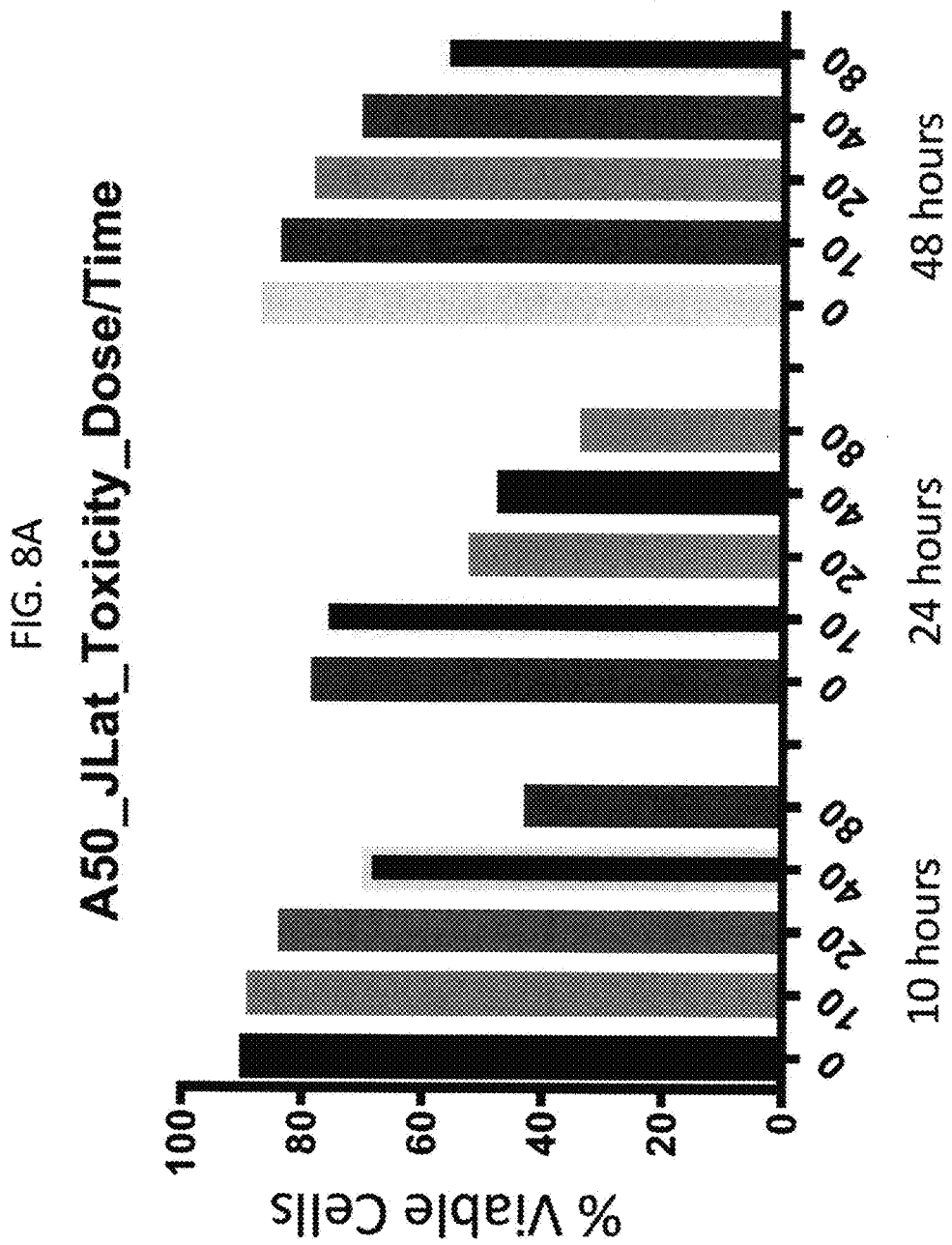

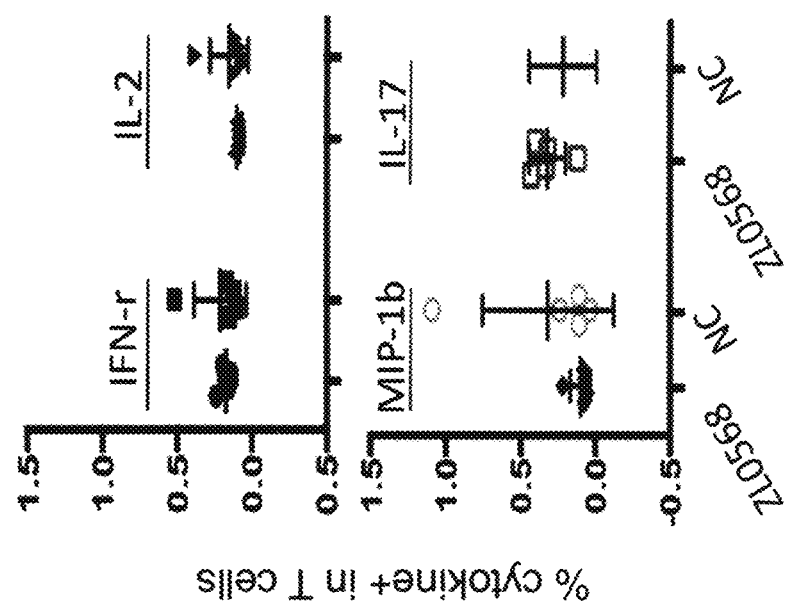

EPAC1 ACTIVATORS AS HIV LATENCY REVERSAL AGENTS (LRA)

CROSS-REFERENCE TO RELATED APPLICATIONS

This application claims the benefit of U.S. Provisional Appl. No. 62/532,545 filed Jul. 14, 2017. The content of the aforesaid application is relied upon and is incorporated by reference herein in its entirety.

FIELD OF THE INVENTION

The field of the invention relates generally to novel EPAC1 activators and the preparation thereof as well as the use of EPAC1 activators as human immunodeficiency virus (HIV) latency reversal agents (LRAs).

BACKGROUND

This background information is provided for the purpose of making information believed by the applicant to be of possible relevance to the present invention. No admission is necessarily intended, nor should it be construed, that any of the preceding information constitutes prior art against the present invention.

HIV causes a global pandemic with >36 million people infected worldwide. HIV infection in the body exists in both an actively replicating state (causing disease symptoms etc.) and a dormant, non-replicating state (which lays in wait). While current anti-retroviral therapy (ART) can efficiently reduce HIV viremia to undetectable levels in infected individuals, it cannot eliminate residual HIV due to establishment of latency. In particular, because latent HIV is not replicating, the anti-retroviral therapy does not eradiate (i.e., cure or eliminate) latent HIV and the patient remains infected with the virus.

While HIV-infected individuals can generally live normal lives under ART, the effects of HIV infection remain significant in viral-suppressed individuals, continuously causing a range of metabolic, immunologic, and neurologic co-morbidities. ART can only affect cells harboring actively replicating virus but not latent reservoirs, which poses a major obstacle to eradicate HIV with current ART-based treatment paradigm. In particular, low levels of HIV replication continuously occur in ART-suppressed individuals and the latent reservoir is capable of rapidly producing infectious virus when ART is discontinued. Therefore, ART treatment requires life-long administration in order to achieve sustained viral suppressed.

Also critically, ART does not fully prevent pathology or restore a normal lifespan in HIV-infected patients. With expanded usage of ART, HIV is becoming more drug resistant, which also markedly erodes the efficacy of ART. Due to these significant limitations, new treatment paradigm that targets latent HIV reservoirs for eradication is needed and has been recognized as a high research priority.

Development of novel strategies targeting latent HIV reservoir has therefore been a high research priority for HIV cure. To date, several categories of LRAs, based on various mechanisms, have been identified and tested in HIV latency cellular models and/or clinical studies, including the histone deacetylase inhibitors (HDACis), bromodomain inhibitors (BETis), PKC agonists, TLR agonists and cytokines.

Current efforts targeting latent HIV for eradication or cure mainly focus on four categories: reactivating latent HIV to 'purge' the virus out of reservoirs (shock), killing of reactivated HIV by strengthening the immune response (kill), keeping the latent reservoirs permanently silenced or targeting latent HIV in CD4+ T cells via novel gene therapy approaches. As the first step of the "shock and kill" approach, discovery and development of effective latency-reversing agents (LRAs) to reactivate latent HIV from reservoirs are critical.

Nevertheless, existing LRAs manifest various significant limitations. To date, a number of latency reversing agents (LRAs), including small pharmacological compounds, have been tested for activating latent HIV in a so-called 'shock and kill' HIV eradication strategy. Existing LRAs, however, demonstrate various significant limitations, such as inefficiency to activate latent HIV in primary cells, limited efficacy in vivo and undesirable toxicity profiles.

Therefore, discovery and development of novel mechanism-based LRAs, especially those also able to activate HIV in primary cells, represent a major knowledge gap and are urgently needed to further expand and complement existing LRAs pool for improving the "HIV Shock and Kill" strategy.

To that end, there is a great need for the discovery and development of novel LRAs, based on new mechanisms of action, to complement existing LRAs for more efficiently activating latent HIV as part of the "shock and kill" approach.

The inventors have surprisingly discovered certain novel EPAC1 activators, including compound ZL0568 (FIG. 2B), that target EPAC for more efficiently activating latent HIV.

SUMMARY

It is to be understood that both the foregoing general description of the invention and the following detailed description are exemplary, and thus do not restrict the scope of the invention.

The inventors have surprisingly discovered certain novel small molecules that may be used as LRAs. In some aspects of the invention these novel small molecules may be used to target EPAC to activate latent HIV.

One aspect of the invention pertains to compounds of Formula I or a pharmaceutically acceptable salt thereof, wherein:

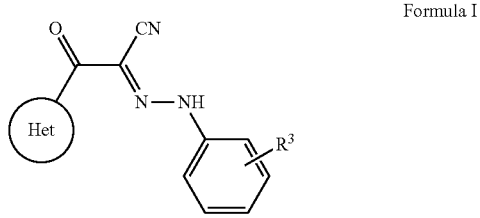

Formula I is a group chosen from:
(i) a substituted or unsubstituted indole of the following structure (Formula Ia):

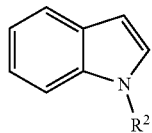

Formula Ia wherein said structure of Formula Ia is attached to the —(C=O)— group of Formula I via the 2-, 3-, 4, 5-, 6-, or 7-position ring carbon atom;
(ii) a classical bioisostere of the indole ring; and
(iii) a non-classical bioisostere of the indole ring chosen from:

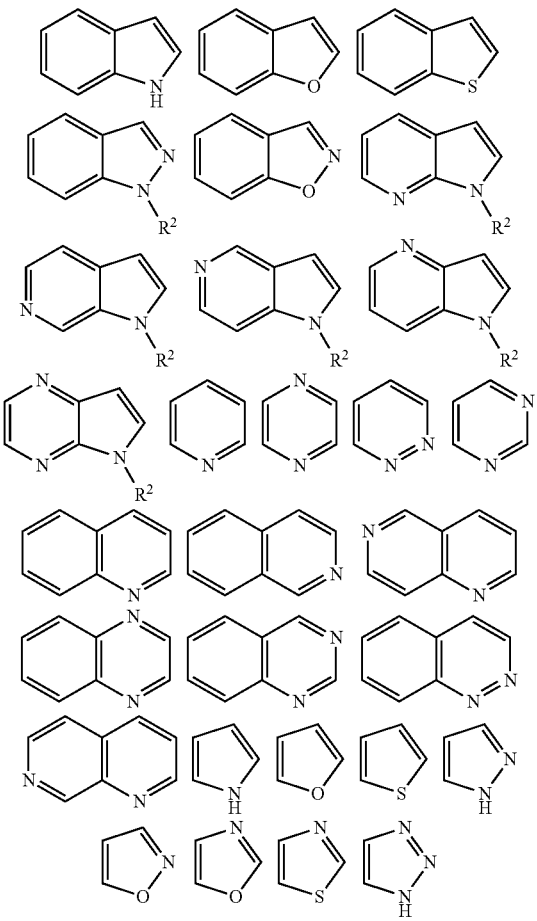

wherein said ring is attached to the —(C=O)— group of Formula I at any available site.
$R^2$ is independently one or more substituents chosen from H, $COR^4$, $SO_2R^4$, —(O=C)$OR^4$, —(O=C)$NHR^4$, $C_1$-$C_6$ alkyl, —$CH_2Ph$, and $C_1$-$C_6$ alkylamine;
$R^3$ is independently one or more substituents chosen from H; $C_1$-$C_6$-alkoxy OH; halide; $NO_2$; $C_1$-$C_6$ alkyl; —$(CH_2)_n$OH, wherein n is 1-8; and a 1,1-dioxidothiomorpholino group;

an optionally fused substituted or unsubstituted group chosen from aryl, heteroaryl, cycloalkyl, β-lactam, γ-lactam, δ-lactam, ε-lactam, and heterocycle;
—(C=O)$OR^4$; —(C=O)$NR^5R^6$; and —$NR^5R^6$; wherein $R^4$, $R^5$, and $R^6$ are independently chosen from H, $C_1$-$C_6$ alkyl, aryl, heteroaryl, cycloalkyl, heterocycle;
$R^4$, $R^5$ and $R^6$ are independently chosen from H, $C_1$-$C_6$ alkyl, $C_1$-$C_7$ cycloalkyl, cycloaryl and cycloheteroaryl.

In some embodiments, the invention encompasses compounds of Formula I, wherein Het is a substituted, or an unsubstituted group, chosen from:

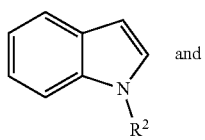

Formula Ia and

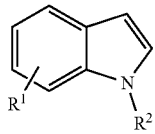

Formula Ib wherein 10 is H, OH, alkyl, aryl, alkoxy, halogen, alkylamino, amino, carboxyl, cyano, or nitro. In certain embodiments, 10 and $R^2$ are independently a $C_1$-$C_6$ alkyl group. In some embodiments, $R^1$ and $R^2$ are independently a methyl group.

In some embodiments, the invention encompasses compounds of Formula I, wherein Het is a substituted, or an unsubstituted group, chosen from:

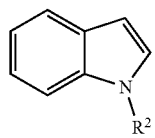

Formula Ia wherein said structure of Formula Ia is attached to the —(C=O)— group of Formula I via the 2-, 3-, 4, 5-, 6-, or 7-position ring carbon atom of Formula Ia.

Another aspect of the invention pertains to generally to use of compounds of the invention to activate latent HIV.

In some embodiments, the invention encompasses a method of activating latent HIV by contacting one or more cells with one or more compounds of the invention, or a pharmaceutically acceptable salt thereof.

In further embodiments, the invention encompasses a method of activating latent HIV by contacting one or more cells with one or more compounds of Formula I, or a pharmaceutically acceptable salt thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 8A. Cellular toxicity of ZL0568 on J-lat cells. Toxicity was measured as % viable cells at Day 1, 2 and 3 after stimulation at various concentrations.

FIG. 8E. Expression of cytokines (% IFN-r, IL-2, MIP-1b or IL-17) in T cells between ZL0568 treatment (10 uM) and NC (24 hours), measured by intracellular cytokine staining.

DETAILED DESCRIPTION

1.0. Definitions

Figure 1:
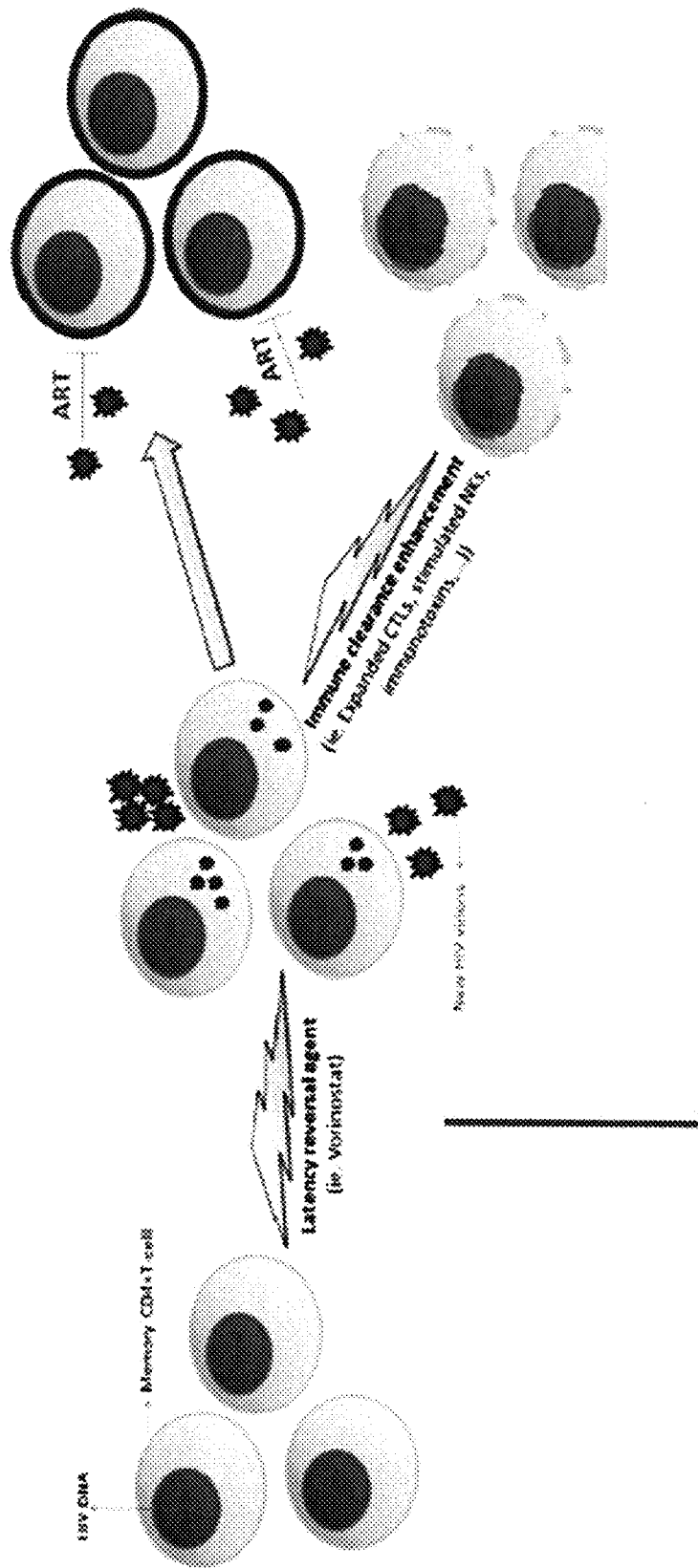
FIG. 1. Traditional strategy for HIV eradication: shock and killing

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated article of manufacture, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

As used herein, the term "tertiary (3°) ring carbon atom" refers to where a ring carbon atom of a "Het" group of Formula I is bonded to three other non-hydrogen atoms, such as carbon (C) or a heteroatom such as nitrogen (N), oxygen (O), or sulfur (S).

As used herein, the terms "cell" and "cells" refer to any types of cells from any animal, such as, without limitation, rat, mice, monkey, and human.

The term "salt" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These can include cations based on the alkali and alkaline earth metals, such as sodium, lithium, potassium, calcium, magnesium, and the like, as well as non-toxic ammonium, tetramethylammonium, tetraethylammonium, methylamine, dimethylamine, trimethylamine, triethylamine, ethylamine and the like (See, for example, S. M. Berge et al., "Pharmaceutical Salts," J. Pharm. Sci., 1977, 66:1-19, which is incorporated herein by reference in its entirety).

The terms "bioisostere", "bioisosteric replacement", "bioisosterism" and closely related terms as used herein have the same meanings as those generally recognized in the art. Bioisosteres are atoms, ions, or molecules in which the peripheral layers of electrons can be considered identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include —$(CH_2)_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

A "carboxylic acid" group refers to a $CO_2H$ group.

An "alkynyl group" refers to a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. In some embodiments, "alkynyl group" refers to an alkynyl chain, which is 2 to 10 carbon atoms in length. In other embodiments, "alkynyl group" refers to an alkynyl chain, which is more 2 to 8 carbon atoms in length. In further embodiments, "alkynyl group" refers to an alkynyl chain, which is from 2 to 4 carbon atoms in length.

An "amido" group refers to an —$CONH_2$ group. An alkylamido group refers to an —CONHR group wherein R is a straight chained, or branched alkyl. In some embodiments, R may be taken together with the —(C=O)— group to form a ring, which may be fused with, or bonded to, to a substituted or unsubstituted aryl, heteroaryl, or heterocyclic ring.

A dialkylamido group refers to an —CONRR' group wherein R and R' are may straight-chained, or branched, alkyl or may be taken together to form a ring, which may be fused with, or bonded to, to a substituted or unsubstituted aryl, heteroaryl, or heterocyclic ring.

The term "halogen" or "halo" or "halide" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects, the optional substituents may be further substituted with one or more substituents independently selected from: halogen, nitro, cyano, hydroxy, amino, mercapto, formyl, carboxy, carbamoyl (—C(O)NR$_2$), unsubstituted alkyl, unsubstituted heteroalkyl, alkoxy, alkylthio, alkylamino, (alkyl)$_2$amino, alkyl sulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, C$_{1-4}$alkyl, phenyl, benzyl, —NH$_2$, —NH(C$_{1-4}$alkyl), —N(C$_{1-4}$alkyl)$_2$, —NO$_2$, —S(C$_{1-4}$alkyl), SO$_2$(C$_{1-4}$alkyl), —CO$_2$(C$_{1-4}$alkyl), and —O(C$_{1-4}$alkyl).

Numbering of Indole Ring Moiety:

For the purposes of this application, the indole moiety is numbered as follows:

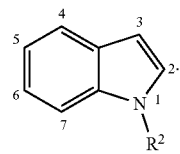

Numbering of Lactam Ring Moiety:

In general, the purposes of this application, for numbering for a lactam moiety, the nitrogen atom is the 1-position, the C=O is numbered at the 2-position and the remaining ring atoms are numbered accordingly. For example, the δ-lactam ring moiety is numbered as follows:

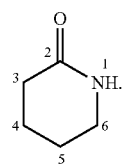

Numbering of the Aryl Group of Formula I Scaffold

In general, the purposes of this application, for numbering of the aryl group of Formula I scaffold:

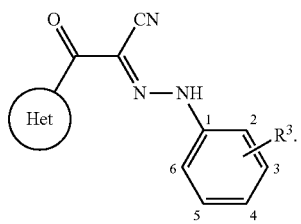

2.0. Compounds

The inventors have surprisingly discovered certain novel small molecules that may be used as LRAs. In some aspects of the invention, compounds of the invention may be used to target EPAC. In certain aspects of the invention, compounds of the invention may be used to target EPAC to activate latent HIV. In other aspects of the invention, compounds of the invention may be used to activate latent HIV.

One aspect of the invention pertains to compounds of Formula I, or pharmaceutically acceptable salts thereof wherein:

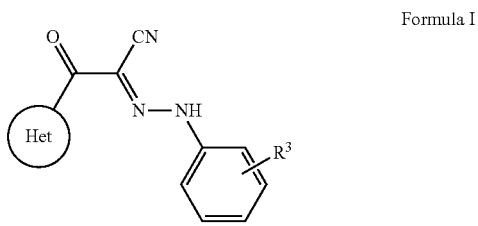

Formula I

is a group chosen from:
(i) a substituted or unsubstituted indole of the following structure (Formula Ia):

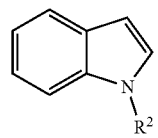

Formula Ia wherein said structure of Formula Ia is attached to the —(C=O)— group of Formula I via the 2-, 3-, 4, 5-, 6-, or 7-position ring carbon atom of Formula Ia;
(ii) a classical bioisostere of the indole ring; and
(iii) a non-classical bioisostere of the indole ring chosen from:

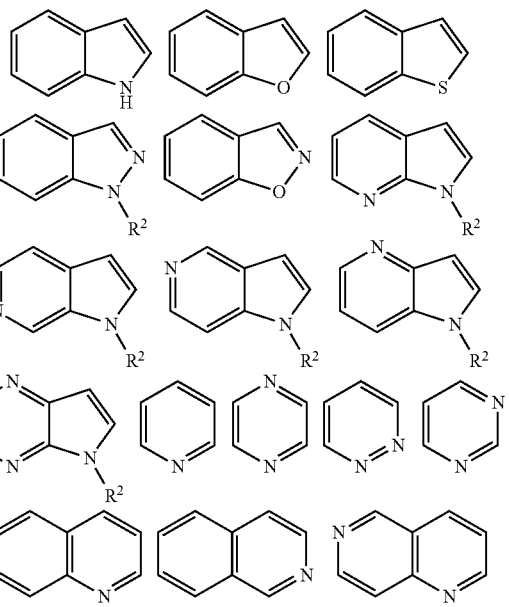

-continued

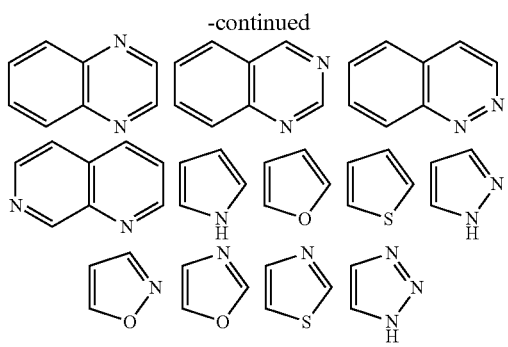
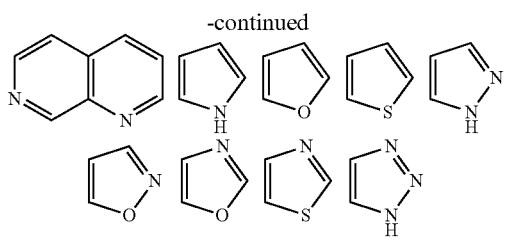

wherein said ring is attached to the —(C=O)— group of Formula I at any available site.

R² is independently one or more substituents chosen from H, COR⁴, SO₂R⁴, —(O=C)OR⁴, —(O=C)NHR⁴, $C_1$-$C_6$ alkyl, —CH₂Ph, and $C_1$-$C_6$ alkylamine;

R³ is independently one or more substituents chosen from H; $C_1$-$C_6$-alkoxy; OH; halide; NO₂; $C_1$-$C_6$ alkyl; —(CH₂)$_n$OH, wherein n is 1-8; and a 1,1-dioxidothiomorpholino group;

an optionally fused substituted or unsubstituted group chosen from aryl, heteroaryl, cycloalkyl, β-lactam, γ-lactam, δ-lactam, ε-lactam, and heterocycle;

—(C=O)OR⁴; —(C=O)NR⁵R⁶; and —NR⁵R⁶; wherein R⁴, R⁵, and R⁶ are independently chosen from H, C1-C6 alkyl, aryl, heteroaryl, cycloalkyl, heterocycle;

R⁴, R⁵ and R⁶ are independently chosen from H, $C_1$-$C_6$ alkyl, $C_1$-$C_7$ cycloalkyl, cycloaryl and cycloheteroaryl.

In some embodiments, the invention encompasses where Het is a non-classical bioisostere of the indole ring chosen from:

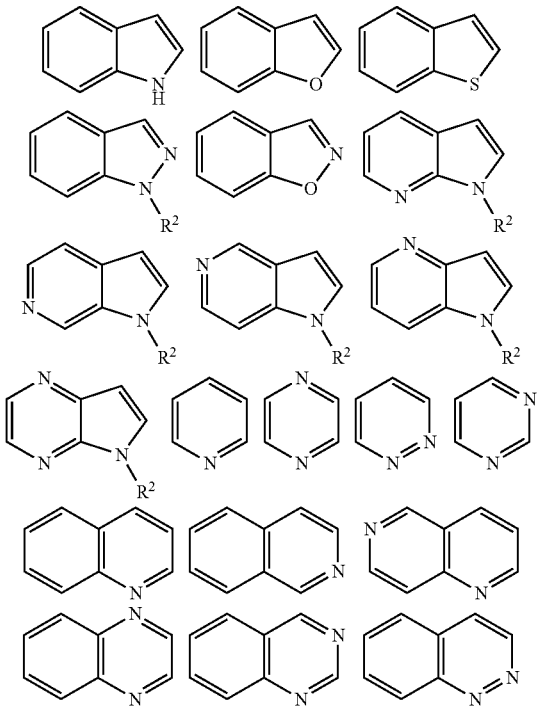

wherein said ring is attached to the —(C=O)— group of Formula I at any available site. In further embodiments, said ring is attached to the —(C=O)— group of Formula I via a ring carbon or a heteroatom. In further embodiments, said ring is attached to the —(C=O)— group of Formula I via a tertiary ring carbon, or a heteroatom.

In some embodiments, the invention encompasses compounds of Formula I, wherein Het is a substituted, or an unsubstituted group, chosen from:

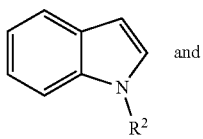

Formula Ia and

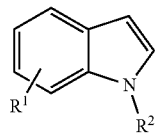

Formula Ib wherein R¹ is H, OH, alkyl, alkoxy, aryl, halogen, carboxyl, cyano, or nitro. In certain embodiments, R¹ is a $C_1$-$C_6$ alkyl group. In some embodiments, R¹ is methyl.

In some embodiments, the —(C=O)— group of Formula I is attached to the 2-, 3-, 4-, 5-, 6-, or 7-position ring carbon atom of said structure of Formula Ia.

In some embodiments, the —(C=O)— group of Formula I is attached to the 2-, 3-, 4-, 5-, 6-, or 7-position ring carbon atom of said structure of Formula Ib.

In certain embodiments, the invention encompasses compounds of Formula I, wherein Het is a Formula Ia group, or a Formula Ib group, wherein R² is H or a $C_1$-$C_6$ alkyl group. In some embodiments, R² is methyl.

In further embodiments, the invention encompasses compounds of Formula I, wherein Het is a substituted, or an unsubstituted, Formula Ia group, or Formula Ib group, wherein the 3-position ring carbon of said group is attached to the —(C=O)— group of Formula I and wherein R² is methyl.

In further embodiments, the invention encompasses compounds of Formula I, wherein Het is a substituted, or an unsubstituted, Formula Ia group, or Formula Ib group, wherein the 2-position ring carbon, or the 3-position ring carbon of said group is bonded to the —(C=O)— group of Formula I.

In further embodiments, the invention encompasses compounds of Formula I, Het is a substituted, or an unsubstituted, Formula Ia group, or Formula Ib group, wherein the 3-position ring carbon of said group is bonded to the —(C=O)— group of Formula I.

In further embodiments, the invention encompasses compounds of Formula I, wherein Het is a substituted, or an unsubstituted group, chosen from:

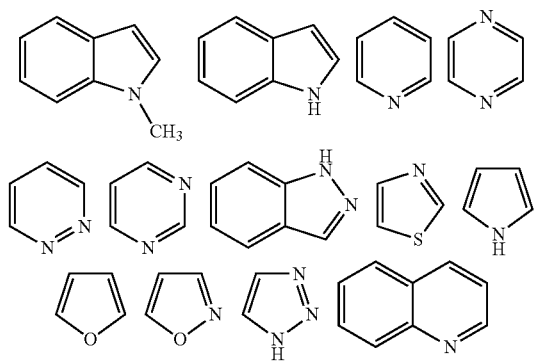

wherein said Het group is attached to the —(C=O)— group of the Formula I moiety via a tertiary (3°) ring carbon atom.

In certain embodiments, the invention encompasses compounds of Formula I, wherein the aryl group of Formula I is optionally fused with $R^3$, wherein $R^3$ is a substituted or unsubstituted group chosen from aryl, heteroaryl, cycloalkyl, β-lactam, γ-lactam, δ-lactam, ε-lactam, and heterocycle.

In some embodiments, the 2,3-ring positions of the aryl group of Formula I is fused with a $R^3$ group. In other embodiments, the 3,4-ring positions of the aryl group of Formula I is fused with a $R^3$ group.

In some embodiments, the inventions encompasses compounds of Formula I, wherein $R^3$ is an optionally substituted or unsubstituted ring (fused with the phenyl ring) chosen from aryl, heteroaryl, cycloalkyl, β-lactam, γ-lactam, δ-lactam, ε-lactam, and heterocycle.

In some embodiments, the invention encompasses compounds of Formula I, wherein $R^3$ is δ-Lactam, and wherein the 4, 5-ring carbons of the lactam ring are fused with the aryl group of Formula I. In further embodiments, the 3,4-ring positions of the aryl group of Formula I are fused with the 4, 5-ring carbons of the lactam ring.

In other embodiments, the 2,3-ring positions of the aryl group of Formula I are fused with the 4, 5-ring carbons of the lactam ring.

In further embodiments, the invention encompasses compounds of Formula I, wherein $R^3$ is δ-Lactam, and wherein the 4, 5-ring carbons of the lactam ring are fused with the aryl group of Formula I.

In certain embodiments, the compound of Formula I is one of:

| Structure (compound number/identifier) | Chemical Name (compound number/identifier) |
|---|---|
| ZL0696 | (E)-N-(2-Chlorophenyl)-2-(1-methyl-1H-indol-3-yl)-2-oxoacetohydrazonoyl cyanide (ZL0696) |
| ZL0568 | (E)-N-(4-chloro-3-(trifluoromethyl)phenyl)-2-(1-methyl-1H-indol-3-yl)-2-oxoacetohydrazonoyl cyanide (ZL0568) |
| ZL0697 | (E)-N-(3-Chlorophenyl)-2-(1-methyl-1H-indol-3-yl)-2-oxoacetohydrazonoyl cyanide (ZL0697) |

| Structure (compound number/identifier) | Chemical Name (compound number/identifier) |
|---|---|
| 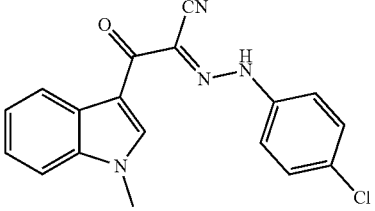<br>ZL0698 | (E)-N-(4-Chlorophenyl)-2-(1-methyl-1H-indol-3-yl)-2-oxoacetohydrazonoyl cyanide (ZL0698) |
| 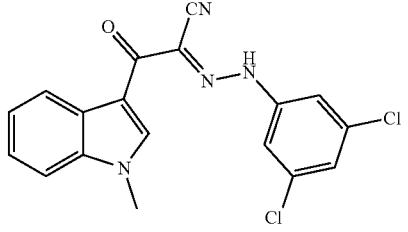<br>ZL0699 | (E)-N-(3,5-Dichlorophenyl)-2-(1-methyl-1H-indol-3-yl)-2-oxoacetohydrazonoyl cyanide (ZL0699) |
| 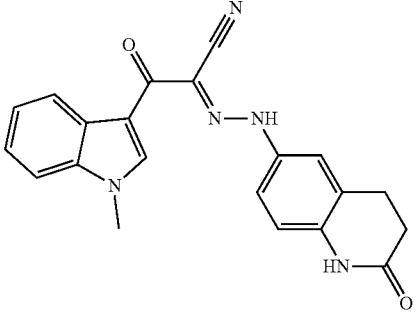<br>ZL06100 | (E)-2-(1-Methyl-1H-indol-3-yl)-2-oxo-N-(2-oxo-1,2,3,4-tetrahydroquinolin-6-yl)acetohydrazonoyl cyanide (ZL06100) |
| 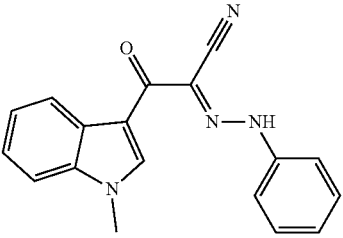<br>ZL0701 | (E)-2-(1-Methyl-1H-indol-3-yl)-2-oxo-N-phenylacetohydrazonoyl cyanide (ZL0701) |
| 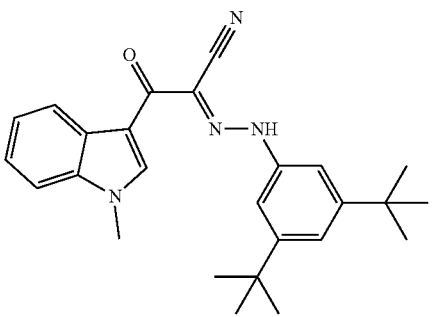<br>ZL0702 | (E)-N-(3,5-Di-tert-butylphenyl)-2-(1-methyl-1H-indol-3-yl)-2-oxoacetohydrazonoyl cyanide (ZL0702) |

-continued

| Structure (compound number/identifier) | Chemical Name (compound number/identifier) |
|---|---|
| ZL0703 | (E)-2-(1-Methyl-1H-indol-3-yl)-2-oxo-N-(3,4,5-trimethoxyphenyl)acetohydrazonoyl cyanide (ZL0703) |
| ZL0704 | (E)-N-(3,5-Bis(trifluoromethyl)phenyl)-2-(1-methyl-1H-indol-3-yl)-2-oxoacetohydrazonoyl cyanide (ZL0704) |
| ZL0705 | (E)-2-(1-Methyl-1H-indol-3-yl)-2-oxo-N-(3,4,5-trifluorophenyl)acetohydrazonoyl cyanide (ZL0705) |
| ZL0706 | (E)-2-(1-Methyl-1H-indol-3-yl)-2-oxo-N-(3-(trifluoromethyl)phenyl)acetohydrazonoyl cyanide (ZL0706) |

| Structure (compound number/identifier) | Chemical Name (compound number/identifier) |
|---|---|
| ZL0707 | (E)-N-(3-Methoxyphenyl)-2-(1-methyl-1H-indol-3-yl)-2-oxoacetohydrazonoyl cyanide (ZL0707) |
| ZL0708 | (E)-N-(3-(Hydroxymethyl)phenyl)-2-(1-methyl-1H-indol-3-yl)-2-oxoacetohydrazonoyl cyanide (ZL0708) |
| ZL0710 | (E)-N-(4-(1,1-Dioxidothiomorpholino)phenyl)-2-(1-methyl-1H-indol-3-yl)-2-oxoacetohydrazonoyl cyanide (ZL0710) |
| ZL0711 | (E)-N-(3-Fluoro-5-(trifluoromethyl)phenyl)-2-(1-methyl-1H-indol-3-yl)-2-oxoacetohydrazonoyl cyanide (ZL0711) |

-continued

| Structure (compound number/identifier) | Chemical Name (compound number/identifier) |
|---|---|
| ZL0712 | (E)-N-(3-Chloro-5-(trifluoromethyl)phenyl)-2-(1-methyl-1H-indol-3-yl)-2-oxoacetohydrazonoyl cyanide (ZL0712) |
| ZL0713 | (E)-N-(4-Chloro-3-fluorophenyl)-2-(1-methyl-1H-indol-3-yl)-2-oxoacetohydrazonoyl cyanide (ZL0713) |
| ZL0714 | (E)-N-(3,4-Dichlorophenyl)-2-(1-methyl-1H-indol-3-yl)-2-oxoacetohydrazonoyl cyanide (ZL0714) |
| ZL0570 | (E)-2-(benzofuran-3-yl)-N-(3,5-dichlorophenyl)-2-oxoacetohydrazonoyl cyanide (ZL0570) |
| ZL0744 | (E)-N-(4-chloro-3-(trifluoromethyl)phenyl)-2-(1H-indol-3-yl)-2-oxoacetohydrazonoyl cyanide (ZL0744) |

| Structure<br>(compound number/identifier) | Chemical Name<br>(compound number/identifier) |
|---|---|
| 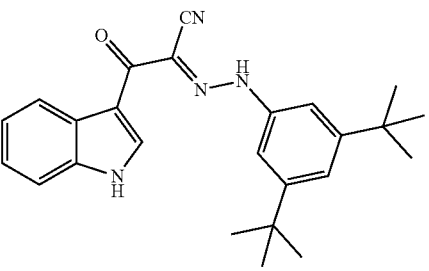<br>ZL0745 | (E)-N-(3,5-di-tert-butylphenyl)-2-(1H-indol-3-yl)-2-oxoacetohydrazonoyl cyanide<br>(ZL0745) |
| 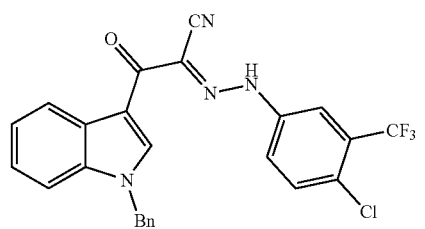<br>ZL0755 | (E)-2-(1-benzyl-1H-indol-3-yl)-N-(4-chloro-3-(trifluoromethyl)phenyl)-2-oxoacetohydrazonoyl cyanide<br>(ZL0755) |
| 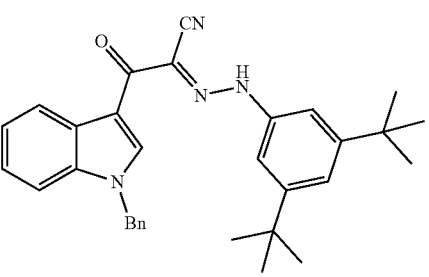<br>ZL0756 | (E)-2-(1-benzyl-1H-indol-3-yl)-N-(3,5-di-tert-butylphenyl)-2-oxoacetohydrazonoyl cyanide<br>(ZL0756) |
| 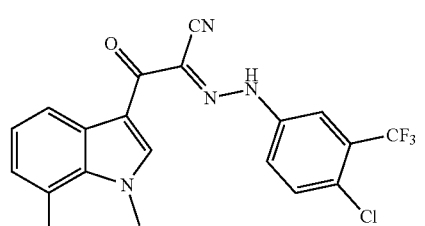<br>ZL0759 | (E)-N-(4-chloro-3-(trifluoromethyl)phenyl)-2-(1,7-dimethyl-1H-indol-3-yl)-2-oxoacetohydrazonoyl cyanide<br>(ZL0759) |
| 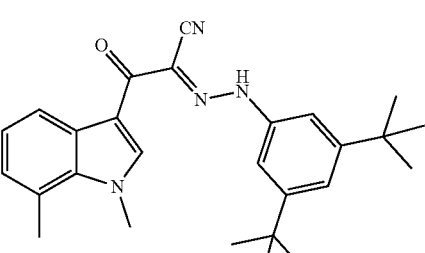<br>ZL0760 | (E)-N-(3,5-di-tert-butylphenyl)-2-(1,7-dimethyl-1H-indol-3-yl)-2-oxoacetohydrazonoyl cyanide<br>(ZL0760) |

| Structure (compound number/identifier) | Chemical Name (compound number/identifier) |
|---|---|
| ZL0762 | (E)-2-(5-cyano-1H-indol-3-yl)-N-(3,5-di-tert-butylphenyl)-2-oxoacetohydrazonoyl cyanide (ZL0762) |
| ZL0769 | (E)-N-(3,5-di-tert-butylphenyl)-2-(5-nitro-1H-indol-3-yl)-2-oxoacetohydrazonoyl cyanide (ZL0769) |
| ZL0770 | (E)-N-(4-chloro-3-(trifluoromethyl)phenyl)-2-(4-cyano-1-methyl-1H-indol-3-yl)-2-oxoacetohydrazonoyl cyanide (ZL0770) |
| ZL0772 | (E)-2-(4-cyano-1-methyl-1H-indol-3-yl)-N-(3,5-di-tert-butylphenyl)-2-oxoacetohydrazonoyl cyanide (ZL0772) |
| ZL0774 | (E)-2-(5-cyano-1-methyl-1H-indol-3-yl)-N-(3,5-di-tert-butylphenyl)-2-oxoacetohydrazonoyl cyanide (ZL0774) |

| Structure (compound number/identifier) | Chemical Name (compound number/identifier) |
|---|---|
| 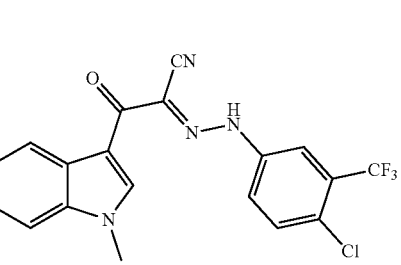<br>ZL0775 | (E)-N-(4-chloro-3-(trifluoromethyl)phenyl)-2-(5-cyano-1-methyl-1H-indol-3-yl)-2-oxoacetohydrazonoyl cyanide (ZL0775) |
| 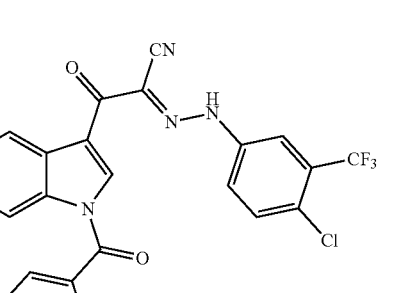<br>PW0175 | (E)-2-(1-Benzoyl-1H-indol-3-yl)-N-(4-chloro-3-(trifluoromethyl)phenyl)-2-oxoacetohydrazonoyl cyanide (PW1075) |

2.1. Synthesis of Compounds of the Invention

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

Certain embodiments of the invention (for example, series A1, also referred to herein as Formula II) may be synthesized (see Scheme 1, below) by first generating by derivation of starting material 1, indoles with various substituents. Reaction of compound 1 with one or more reagents, for example, acyl chlorides, sulfonyl chlorides, chloroformates, or isocyanates in the presence of a base, such as sodium hydride (NaH), to produce diversified intermediates 2. Introduction of oxopropanenitrile into compound 2 in the presence of, for example, acetic anhydride ($Ac_2O$) and 2-cyanoacetic acid will yield key intermediates 3. Amine 4 may be transformed into its corresponding diazo salt 5 with HCl and sodium nitrite ($NaNO_2$). The addition reactions between 3 and 5 in the presence of a base, such as sodium acetate (NaOAc) to give compounds of Series A1 (or Formula II).

Furthermore, certain embodiments of the invention (for example, series A2, also referred to herein as Formula I) may be obtained by taking heterocycles 6, which may be classical or non-classical bioisosteres of indole ring, with ester functional group as the starting material, intermediates 7 with side chain of oxopropanenitrile can be obtained using a base, such as sodium hydride (NaH) in the presence of a solvent, such as $CH_3CN$ (acetonitrile). Similarly, the reaction of compounds 5 and 7 may be used to produce compounds of Series A2 (a/k/a Formula I) as shown in Scheme 1:

Scheme 1

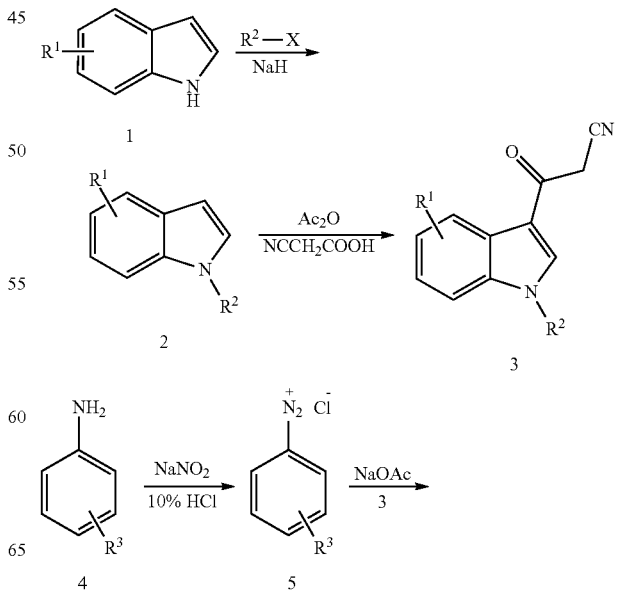

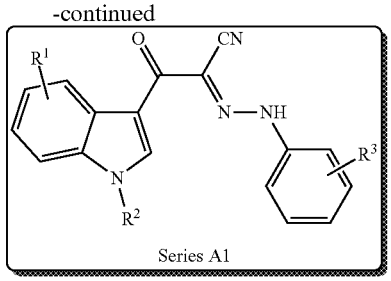

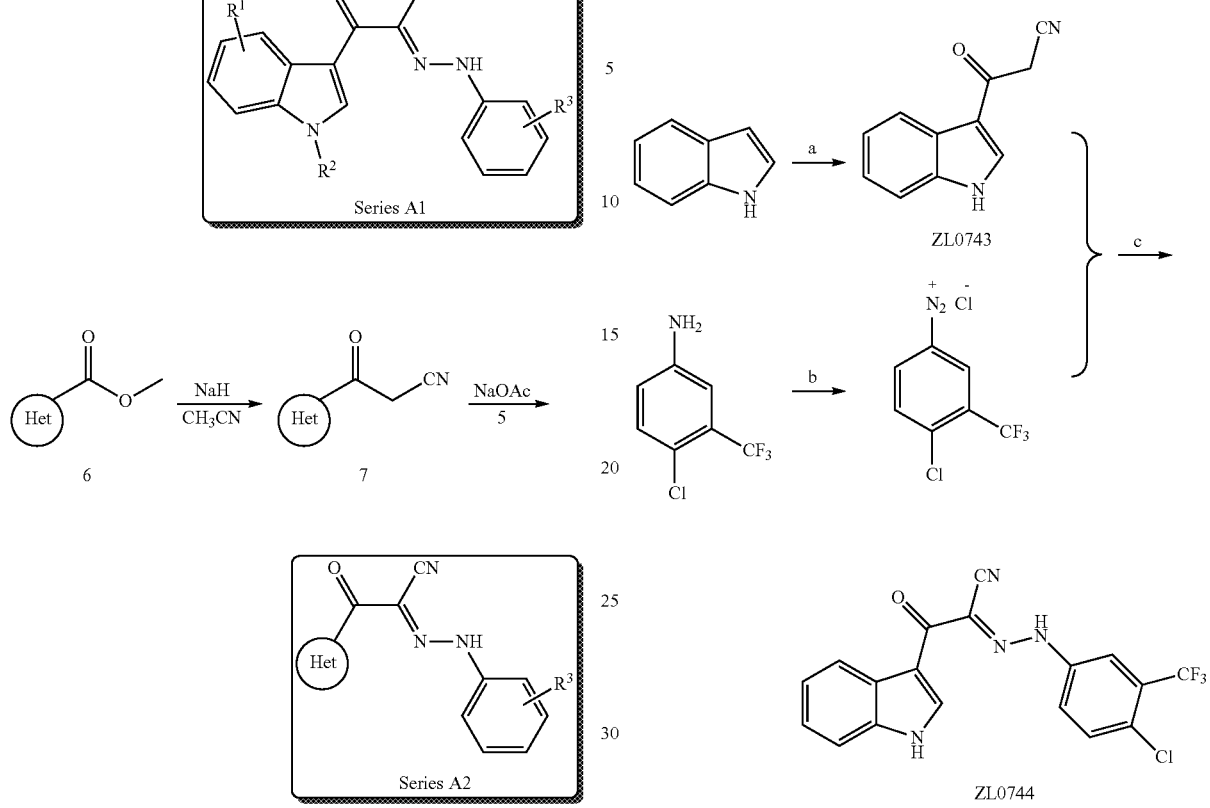

In some embodiments, preparation of certain compounds of the invention may involve a coupling reaction as exemplified by preparation of compound ZL0696 (Scheme 2):

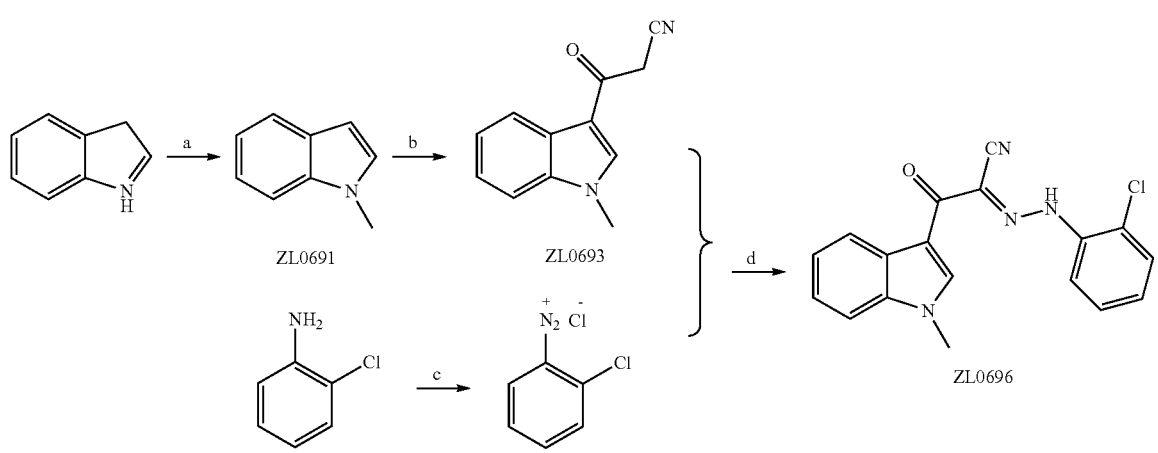

Reagents and conditions: (a) 60% NaH, CH₃I, THF, rt, 12 h, put into next step directly. (b) NCCH₂COOH, Ac₂O, 85° C., 10 min, 68% for two steps; (c) 10% HCl, NaNO₂, H₂O, rt; (e) NaOAc, EtOH/DMF, rt, quant.

In another embodiment, preparation of certain compounds of the invention may involve a coupling reaction as exemplified by preparation of compound ZL0744 (Scheme 3):

In another embodiment, preparation of certain compounds of the invention may involve a coupling reaction as exemplified by preparation of compound ZL0755 (Scheme 4):

Scheme 4

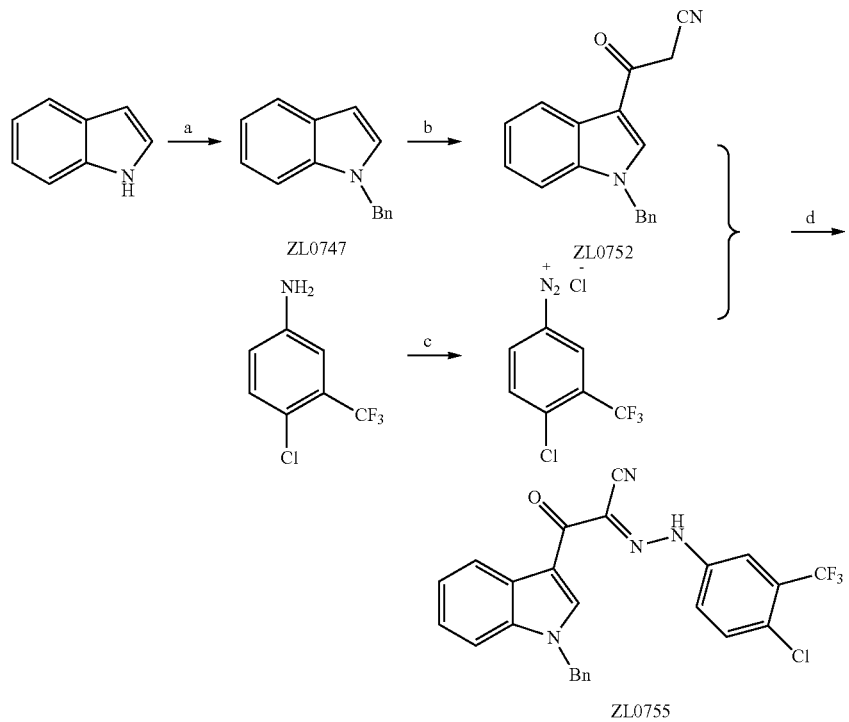

Reagents and conditions: (a) 60% NaH, BnBr, DMF, rt, 12 h, put into next step directly.
(b) NCCH₂COOH, Ac₂O, 85° C., 10 min, 67% for two steps; (c) 10% HCl, NaNO₂, H₂O, rt; (e) NaOAc, EtOH/DMF, rt, 73%.

In another embodiment, preparation of certain compounds of the invention may involve a coupling reaction as exemplified by preparation of compound PW0175 (Scheme 5):

Scheme 5

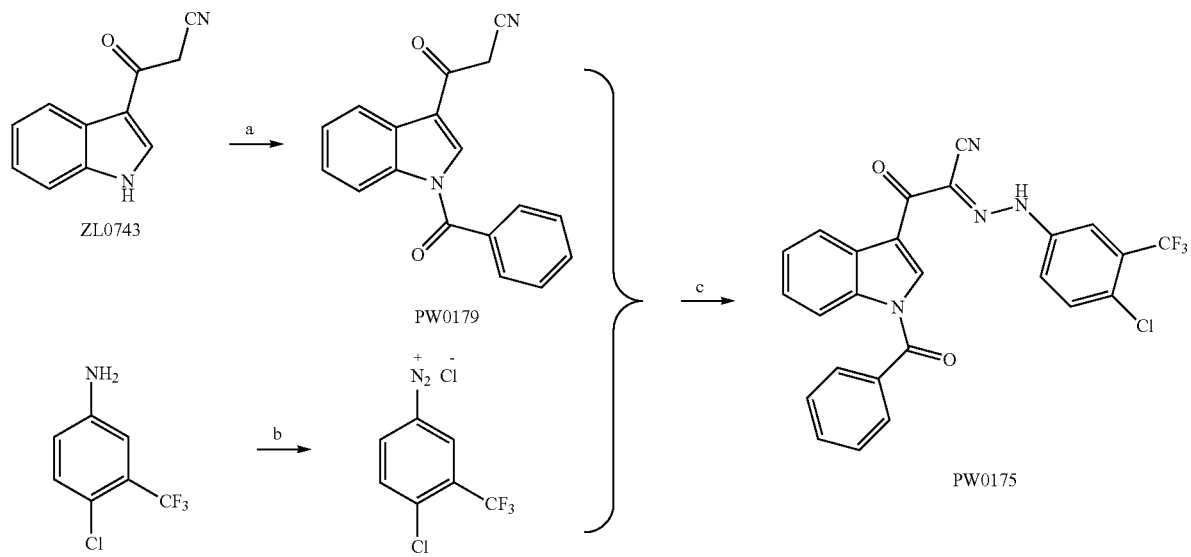

Reagents and conditions: (a) benzoyl chloride, DAMP, NEt₃, 8 h, 51%; (b) 10% HCl, NaNO₂, H₂O, rt; (c) NaOAc, EtOH/DMF, rt, 84%.

3.0. Method of Use

One aspect of the invention pertains to generally to use of compounds of the invention to activate latent HIV.

The inventors utilized a well-characterized, EPAC agonist (007-AM; a cAMP analog) to stimulate J-lat cells and surprisingly discovered that 007-AM can induce significant HIV reactivation (based on GFP expression), whereas EPAC-specific inhibitor ESI-09 had no HIV activation effect; ablation of EPAC (EPAC1) expression by CRISPR/Cas9 abrogated 007-AM-stimulated HIV activation, supporting a functional role of EPAC signaling in this process.

The inventors also surprisingly discovered that compound ZL0568 causes modest level of T-cell activation (FIG. 8D), suggesting that the HIV activating effect of ZL0568 through EPAC very possibly involves some T-cell activation signaling pathways.

In some embodiments, the invention encompasses a method of activating latent HIV by contacting one or more cells with one or more compounds of the invention, or a pharmaceutically acceptable salt thereof.

In further embodiments, the invention encompasses a method of activating latent HIV by contacting one or more cells with one or more compounds of Formula I, or a pharmaceutically acceptable salt thereof.

In further embodiments, the invention encompasses a method of activating latent HIV by contacting one or more cells with one or more compounds chosen from ZL0568 and ZL06100, or a pharmaceutically acceptable salt thereof.

In further embodiments, the invention encompasses a method of activating latent HIV by contacting one or more cells with compound ZL0568, or a pharmaceutically acceptable salt thereof.

In further embodiments, the invention encompasses a method of activating latent HIV by contacting one or more cells with compound ZL06100, or a pharmaceutically acceptable salt thereof.

4.0 Examples

4.1. Discovery of a Novel Compound that can Activate Latent HIV in the J-Lat Cells.

Figure 2A:
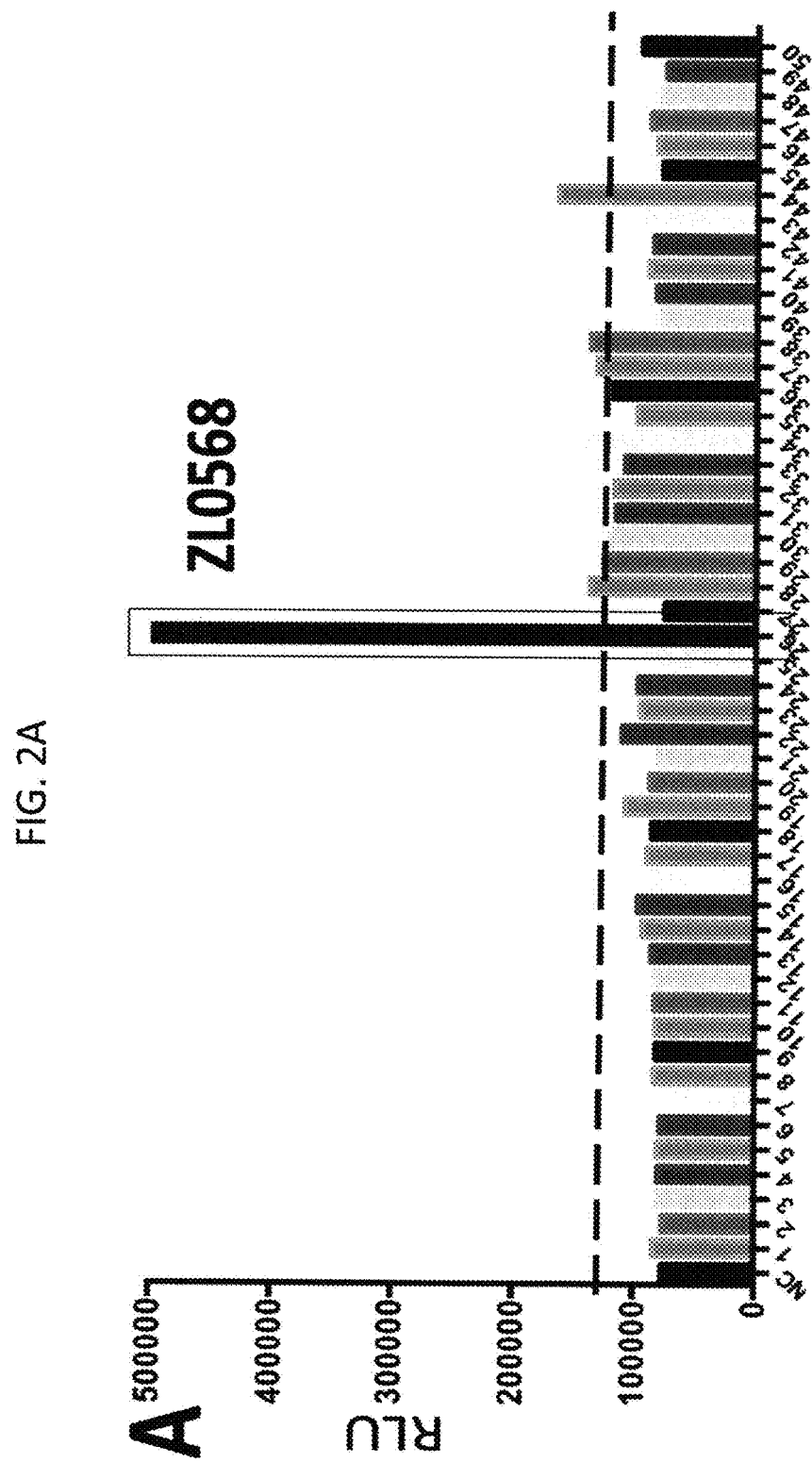
FIG. 2A. Assessment of compound ZL0568, an exemplary embodiment of the invention, for the ability to stimulate GFP expression in J-lat cells. GFP fluorescence intensity was measured by microplate reader.
Figure 2B:
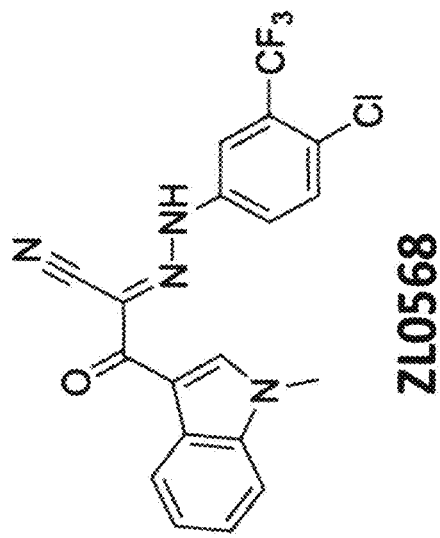
FIG. 2B. Compound ZL0568, an exemplary embodiment of the invention. Compound ZL0568 activated GFP expression.
Figure 2C:
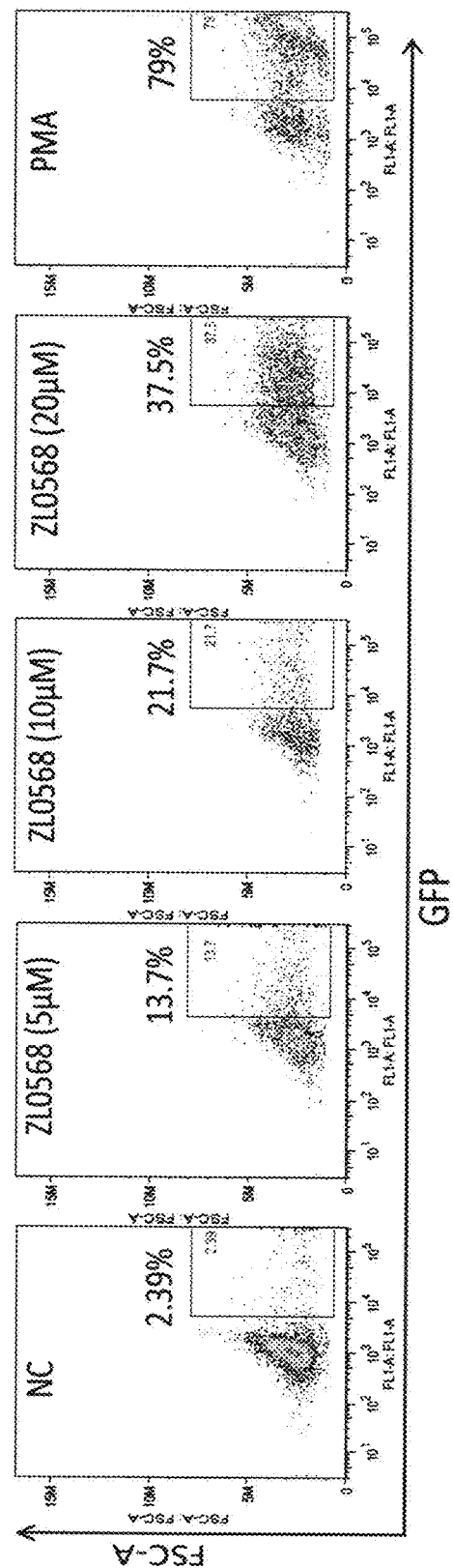
FIG. 2C. Dose-dependent activation of GFP expression in J-lat cells by ZL0568 measured by flow cytometry.
Figure 2D:
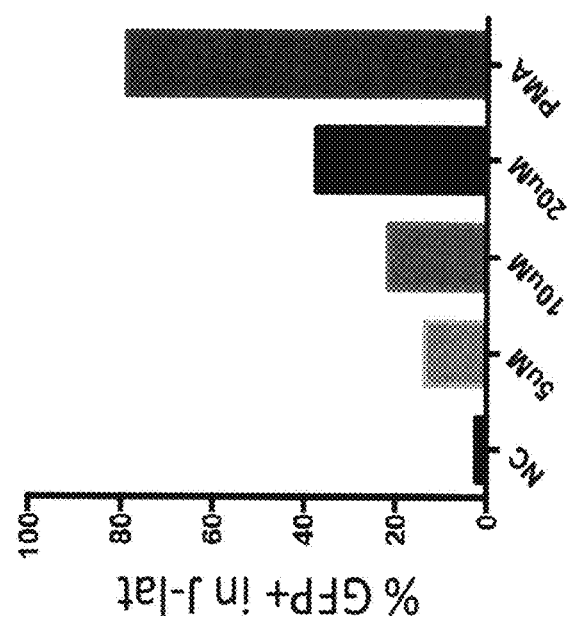
FIG. 2D. Dose-dependent activation of GFP expression in J-lat cells by ZL0568 measured by flow cytometry.

The inventors have discovered compound ZL0568, an exemplary embodiment of the invention, can selectively stimulate significant GFP expression in J-lat cells (FIG. 2A), indicating that this compound may be used to activate latent HIV. Dose-dependent activation of GFP expression by ZL0568 in J-lat cells was confirmed by flow cytometric analysis with an $EC_{50}$ value of 8 μM (in DMSO) (FIG. 2C-D). At this concentration, the compound ZL0568 manifested negligible toxicity to J-lat cells. See e.g., FIG. 8A-E.

Figure 3A:
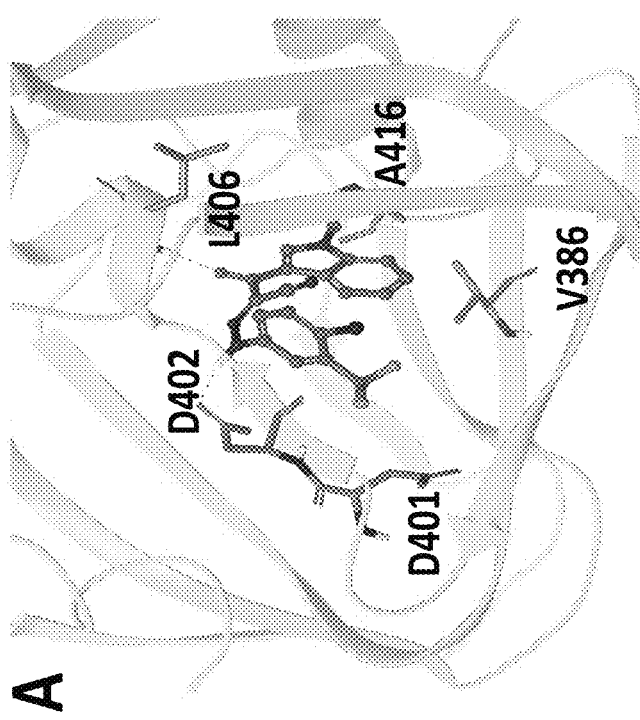
FIG. 3A. Ribbon representation of ZL0568 docked into CBD-B of EPAC (PDB ID: 3CF6). ZL0568 is shown in magenta sticks. Binding site of EPAC is shown in ribbons. Key interaction residues are shown in gray sticks. Hydrogen bond is shown in purple dotted line.
Figure 3B:
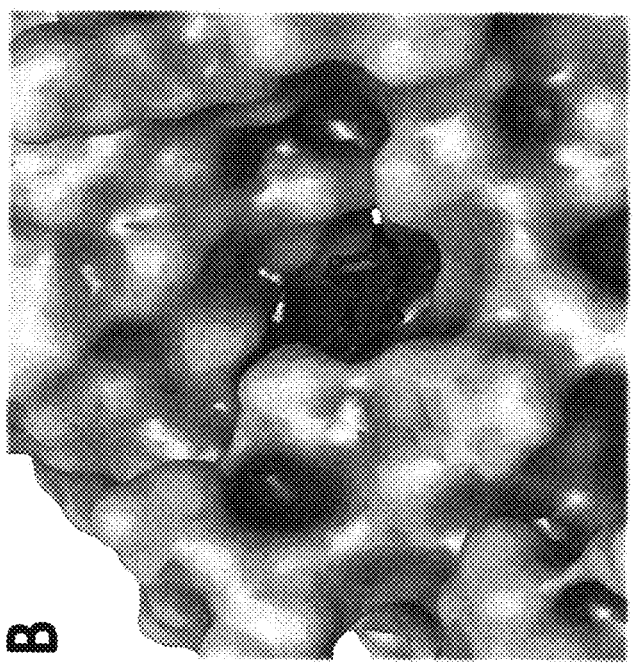
FIG. 3B Surface representation of predicted binding mode.

4.2. Involvement of EPAC in ZL0568-Induced HIV Reactivation (GFP Expression) in J-Lat Cells The inventors sought to explore potential mechanisms or pathways that mediate ZL0568-induced HIV reactivation in J-lat cells. The experiments focused on EPAC signaling. First, to investigate the binding of ZL0568 with EPAC, molecular docking of ZL0568 with cAMP binding domain B (CBD-B) of active EPAC (PDB ID: 3CF6) using the Schrödinger Small-Molecule Drug Discovery Suite was performed. ZL0568 was found to fit well into the functional CBD-B binding pocket of active EPAC. The indole ring and the N-methyl moiety of ZL0568 can form strong hydrophobic interactions with residues V386, L397, L406 and A416 of EPAC. The trifluoromethyl group on phenyl ring of ZL0568 interacts with residues D401 and D402. Moreover, hydrogen bonds are formed between the oxygen atom of the carbonyl group and residues L406, as well as between the nitrogen atom of the linker and residue D402 (FIG. 3A-B).

Figure 3C:
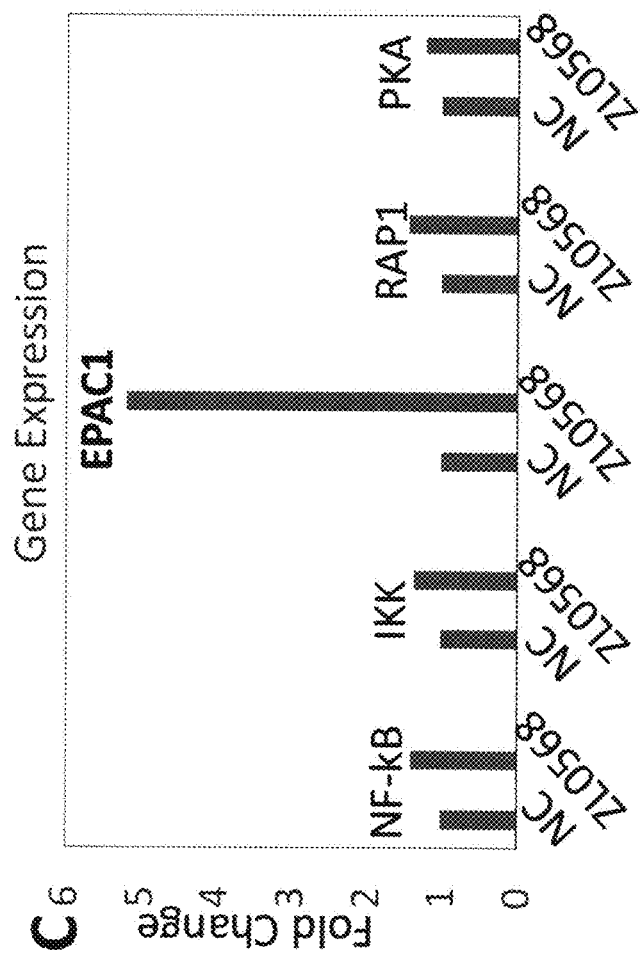
FIG. 3C. Gene expression in J-lat cells with or without ZL0568 stimulation.

Next, the effect of ZL0568 stimulation on gene expression in J-lat cells with a focus on EPAC pathway (EPAC; RAP1), PKA (another intracellular cAMP sensor) and T-cell activation pathway (NF-kB; IKK) was explored, and it was found that only EPAC was selectively up-regulated (FIG. 3C), suggesting a potential feed-back regulatory mechanism for EPAC expression by ZL0568.

Figure 3D:
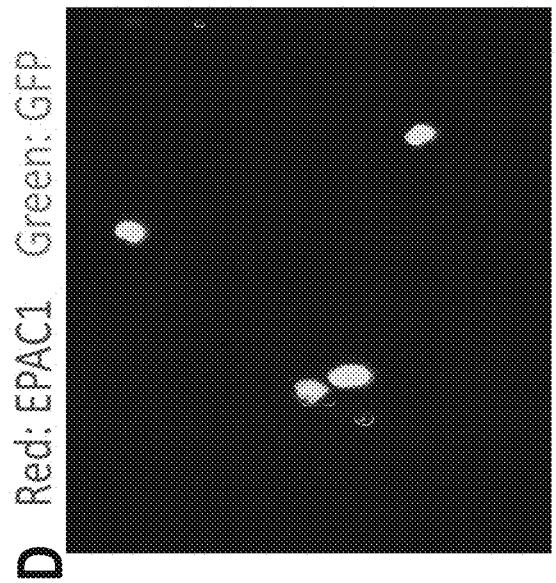
FIG. 3D. Co-expression of GFP (green) and EPAC (red; Alex Fluor 594) in ZL0568-stimulated J-lat cells.
Figure 3E:
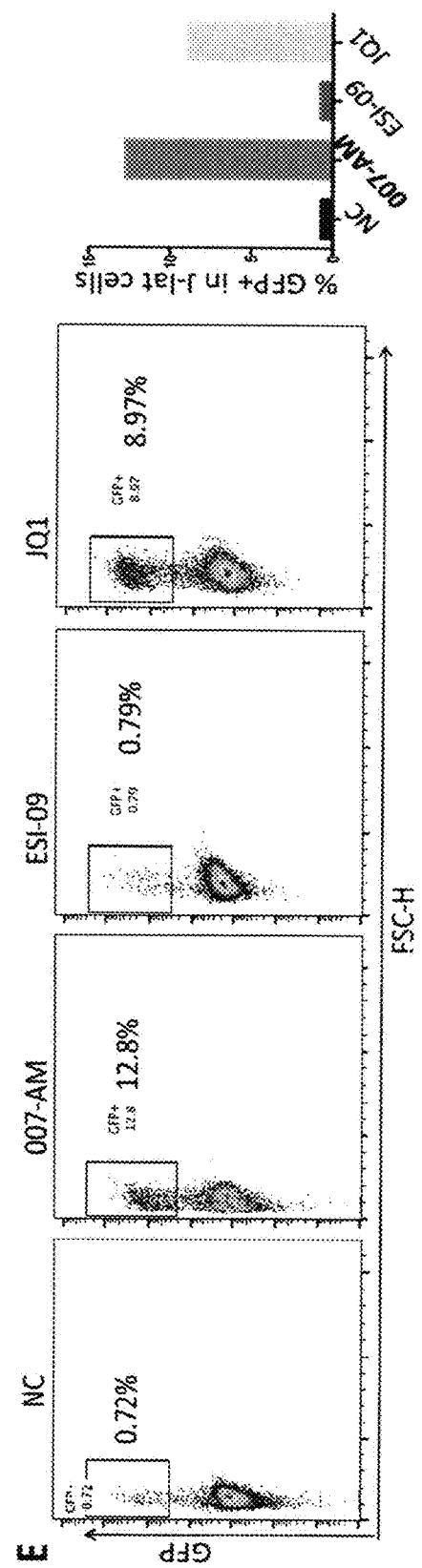
FIG. 3E. Flow cytometric measurement of GFP expression in J-lat cells stimulated with EPAC-activator (007-AM) or inhibitor (ESI-009). Mock (DMSO) or JQ1 stimulation was included as controls.
Figure 3F:
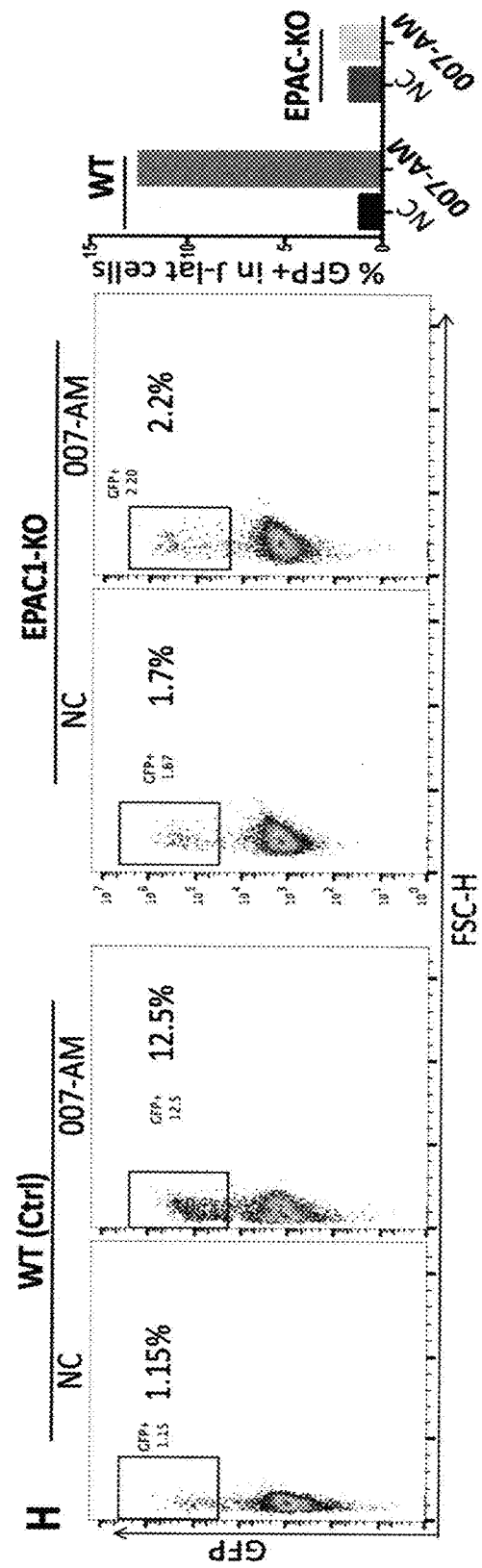
FIG. 3F. Functional involvement of EPAC in 007-AM stimulated HIV reactivation in J-lat cells.

It was also found that EPAC and GFP co-expressed in ZL0568-stimulated cells (FIG. 3D), suggesting a relationship between EPAC and induction of GFP expression following ZL0568 treatment. To further investigate the role of EPAC signaling in HIV reactivation, a well-characterized EPAC activator (007-AM) (47-49) to stimulate J-lat cells was used and showed that 007-AM could induce significant GFP expression (12.8%; 10 M), which was higher than that by JQ1 (8.97%; 10 M) but lower than that by compound ZL0568 (21.7%; 10 M), whereas the EPAC-selective inhibitor ESI-09 had no GFP-activating effect (FIG. 3E).

CRISPR/Cas9 was then used to knock out EPAC expression in J-lat cells and it was found that ablation of EPAC led to marked decrease in 007-AM-stimulated GFP expression, providing strong evidence for functional involvement of EPAC in mediating HIV reactivation in J-lat cells.

4.3. Activating Latent HIV in U-1 Cells Using ZL0568.

Figure 4:
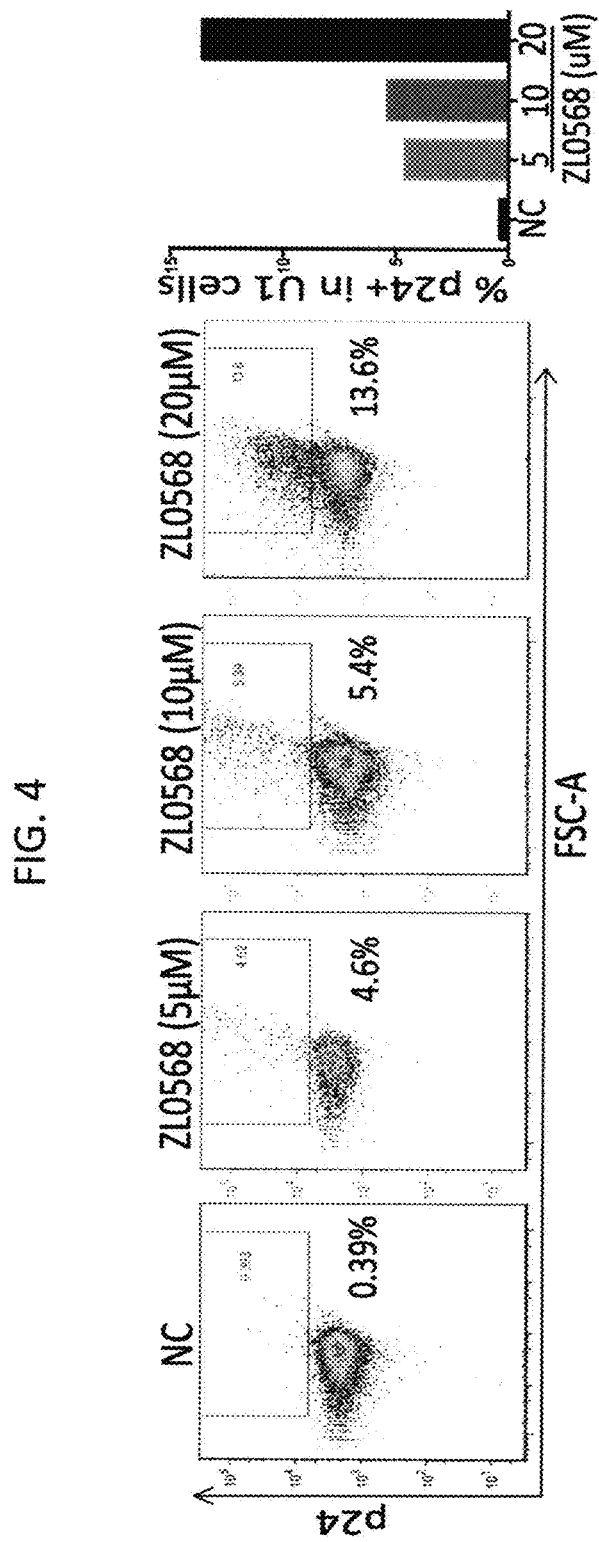
FIG. 4. Activation of latent HIV by compound ZL0568 in U1 cells. U1 cells were stimulated with various concentrations of compound ZL0568 as indicated or mock-stimulated (NC) for 48 hours. Reactivation of latent HIV were examined based on intracellular HIV p24 staining (p24%) by flow cytometry.

Whether or not compound ZL0568, an exemplary embodiment of the invention, can activate latent HIV in human monocytic U1 cells was evaluated. In particular, U1 cells were stimulated with various concentrations of ZL0568 or mock DMSO (NC). Reactivation of latent HIV was measured based on intracellular HIV p24 staining by flow cytometry. It was found that ZL0568 could also stimulate HIV reactivation in U1 cells in a dose-dependent manner, based on p24 expression (FIG. 4).

4.4. Activation of HIV Gene Expression by ZL0568 in PBMC of ART Naïve, Viremic HIV-Infected Individuals A significant limitation for some existing LRAs (e.g. HDACi & BETi) is related to their limited efficacy to activate latent HIV in primary cells (16, 17, 19-21). Whether or not our compound ZL0568 can stimulate HIV gene expression in human PBMC from ART-naïve, viremic HIV-infected individuals was assessed using cells from the RV21, an ART-naïve, HIV infection cohort at the Military HIV Research Program (MHRP). See e.g., Liu F, et al. Sequential Dysfunction and Progressive Depletion of *Candida albicans*-Specific CD4 T Cell Response in HIV-1 Infection. PLoS Pathog 12(6):e1005663 (2016). A widely-used method to detect HIV transcription in cells from infected individuals involves measurement of RNAs containing HIV gag sequences. Since this method lacks a stringent selection for polyadenylated RNAs, it does not exclusively detect fully elongated and correctly processed HIV-1 mRNAs. See e.g., Bullen C K, Laird G M, Durand C M, Siliciano J D, & Siliciano R F, New ex vivo approaches distinguish effective and ineffective single agents for reversing HIV-1 latency in vivo. Nat Med 20(4):425-429 (2014).

Therefore, in addition to Gag, a new PCR assay, established by the Siliciano group, specific for intracellular HIV mRNA using a primer/probe set that detects the 3'-sequence common to all correctly terminated HIV RNAs was employed. See e.g., Bullen C K, Laird G M, Durand C M, Siliciano J D, & Siliciano R F, New ex vivo approaches distinguish effective and ineffective single agents for reversing HIV-1 latency in vivo. Nat Med 20(4):425-429 (2014).

Figure 5A:
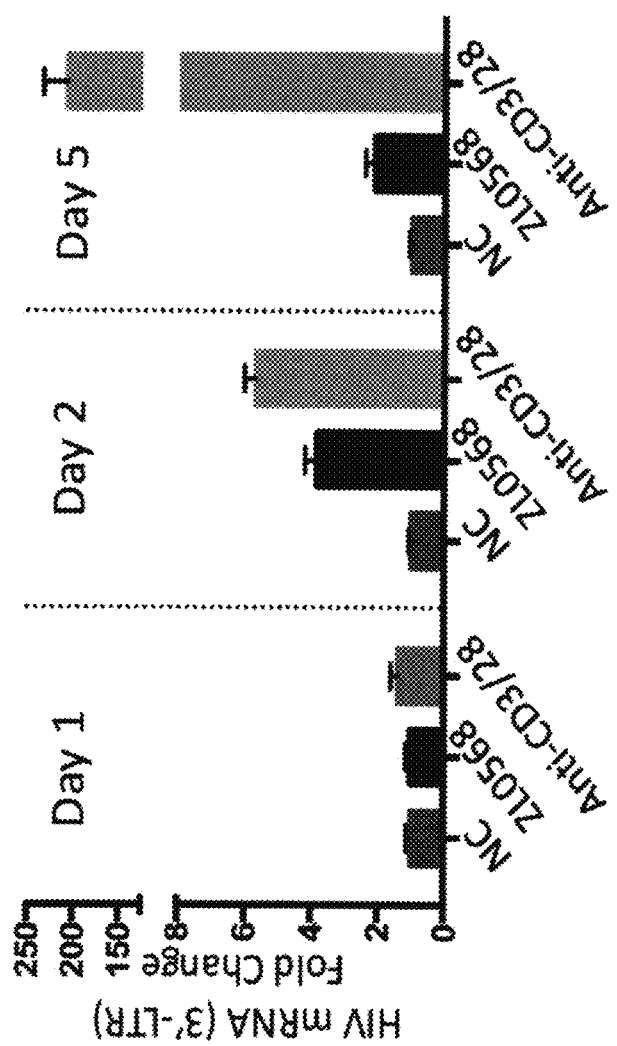
FIG. 5A Activation of HIV gene expression (3' LTR) in a representative RV21 PBMC on Day 1, 2 and 5 after stimulation. The data are shown as fold change to NC.
Figure 5B:
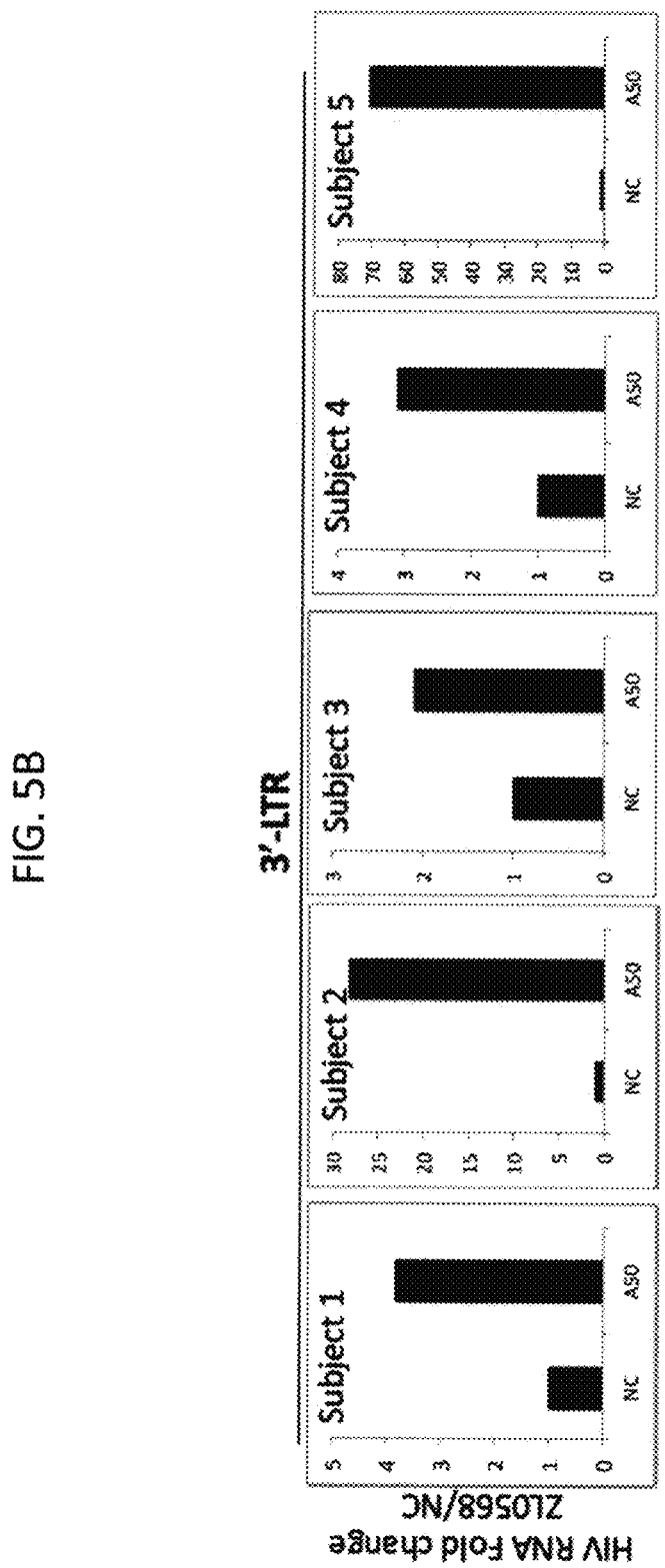
FIG. 5B. Activation of HIV gene expression by ZL0568 for HIV 3'-LTR for multiple RV21 PBMCs.
Figure 5C:
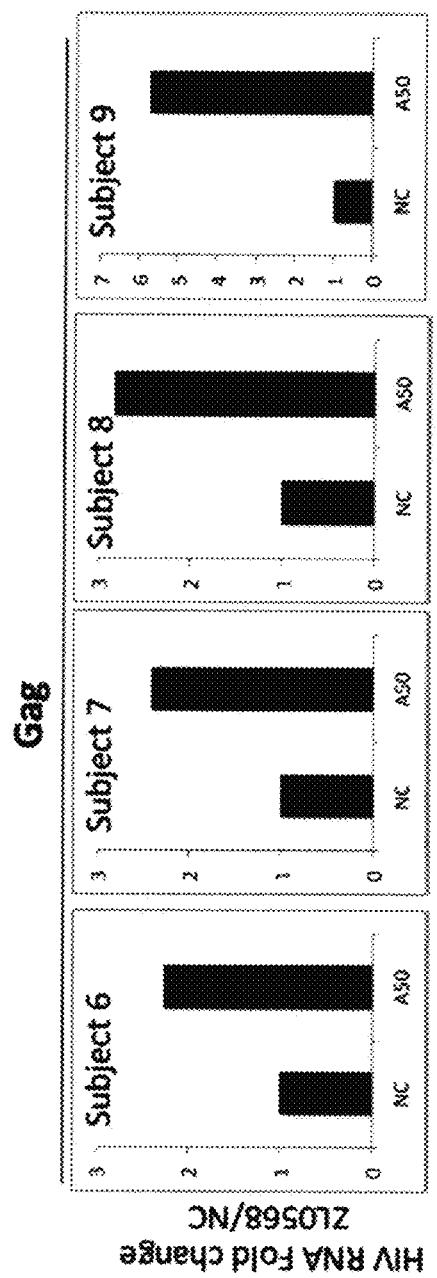
FIG. 5C. Activation of HIV gene expression by ZL0568 for HIV Gag for multiple RV21 PBMCs.
Figure 5D:
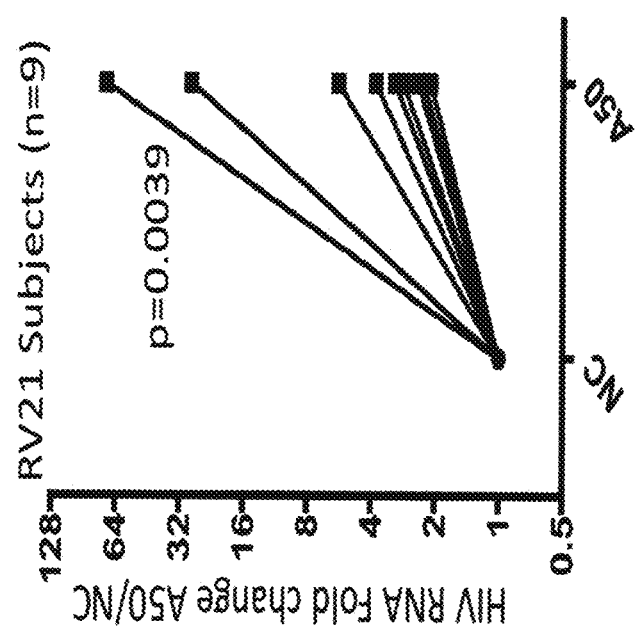
FIG. 5D. Cumulative results for activation of HIV gene expression by ZL0568 compared to NC (3' LTR and Gag) (n=9). p<0.005.

First, HIV gene expression in a representative RV21 PBMC at multiple time points after ZL0568 stimulation was examined and it was found that ZL0568 (10 M) induced HIV 3'-TLR expression on Day 2 after stimulation, which became less significant on Day 5 (FIG. 5A). Focus was then shifted to Day 2 for examining ex vivo activation of HIV by ZL0568 (3'-LTR, n=5, FIG. 5B; Gag, n=4, FIG. 5C) and obtained consistent results from different donors. When analyzing 3'TLR and Gag results together, it was shown that ZL0568 could significantly activate HIV gene expression in ART-naïve, RV21 PBMCs (p<0.005) (FIG. 4E).

4.5. Activation of Latent HIV in PBMC of HAART-Suppressed, Aviremic HIV-Infected Individuals The ability of compound ZL0568 to activate latent HIV in PBMC of ART-suppressed, aviremic HIV-infected subjects was tested. PBMC samples were obtained from the well-established HIV infection cohort from the National NeuroAIDS Tissue Consortium (NNTC) with (66, 67). First, feasibility of using NNTC's cryopreserved PBMC in the experiments was explored by comparing the results from fresh and frozen PBMC of the same subject. It was observed that cell viability and RNA quantity/quality isolated from these cells were comparable between fresh and cryopreserved cells (data not shown). Thus, fresh and cryopreserved PBMC from a representative NNTC subject (ID: 8400337177) were stimulated with compound ZL0568 (10 M) as compared to stimulation with mock (NC) or positive controls (JQ1, Prostratin and PMA; concentrations of positive controls were used as previously reported (21, 25)).

Figure 6A:
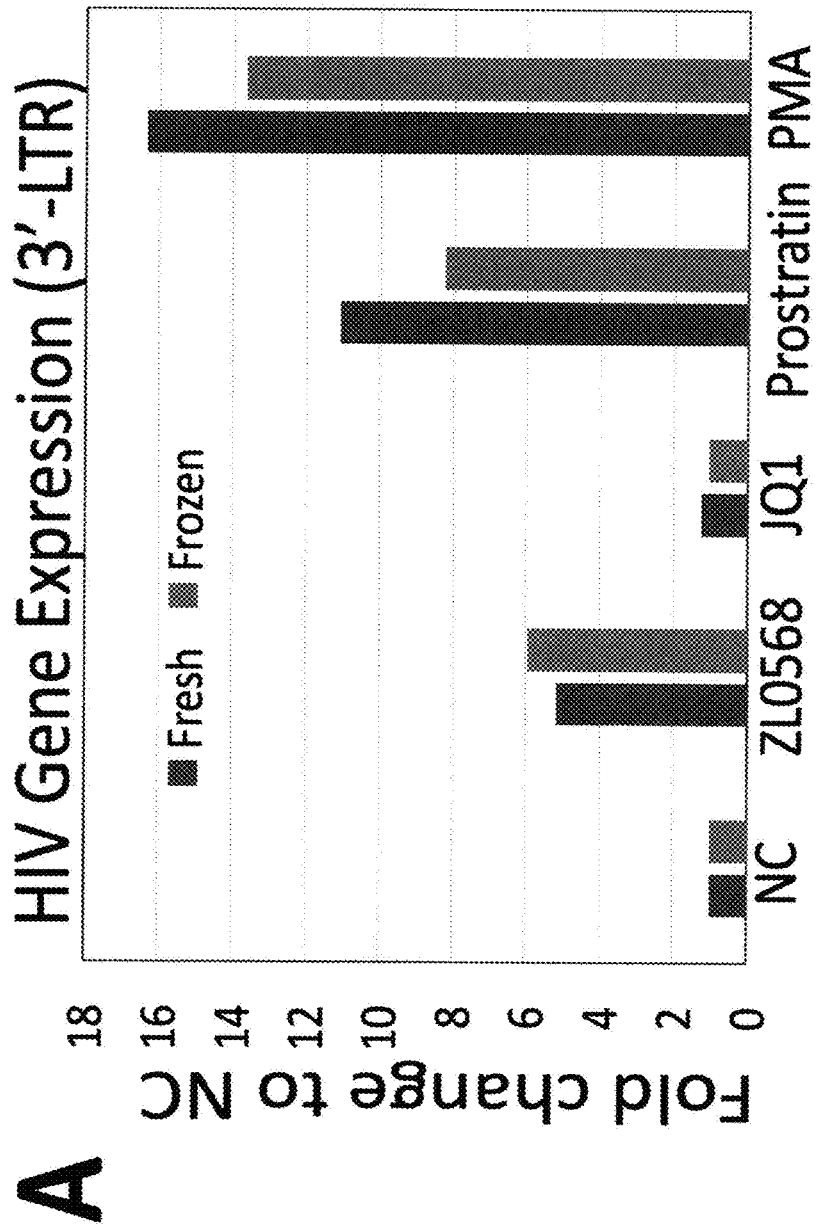
FIG. 6A. Relative HIV gene expression in one representative PBMC following different treatments. Fresh and cryopreserved PBMC of the same donor were compared.
Figure 6B:
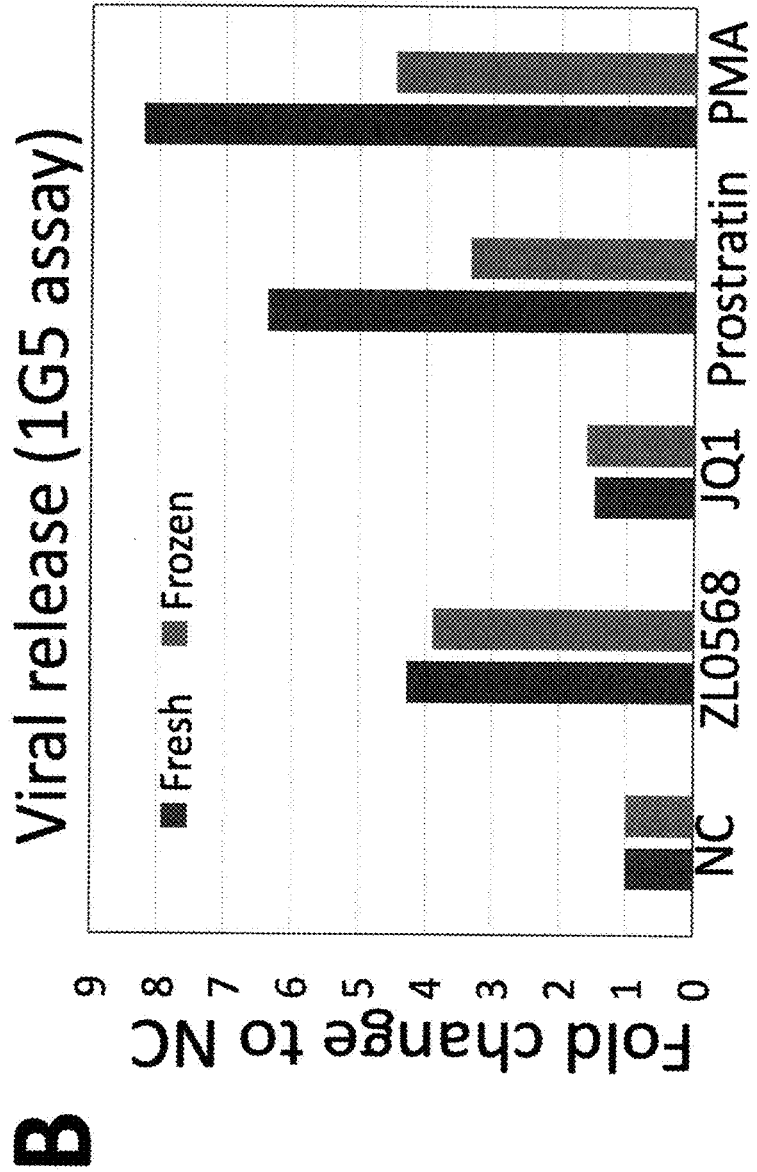
FIG. 6B. Relative viral release in one representative PBMC following different treatments. Fresh and cryopreserved PBMC of the same donor were compared.

It was found that compared to NC, ZL0568 treatment caused significant HIV gene expression, based on PCR quantification of HIV 3'LTR at 48 hours after treatment, in both fresh and frozen PBMCs (FIG. 6A). As important controls, PMA and Prostratin (PKC agonist) also markedly activated HIV gene expression (higher than ZL0568), whereas JQ1 failed to do so in these cells (FIG. 6A), which was consistent with recent reports (21). HIV release in the supernatants of PBMC at 72 hours after treatments using the 1G5 luciferase reporter assay (68, 69) was measured and very similar results were found (FIG. 6B). We noted that although the levels of HIV activation in frozen PBMC were generally lower than those in fresh PBMC, the differences among different treatments were consistently detected (FIG. 6A-B), supporting the feasibility of using NNTC's cryopreserved PBMCs in our system.

Figure 6C:
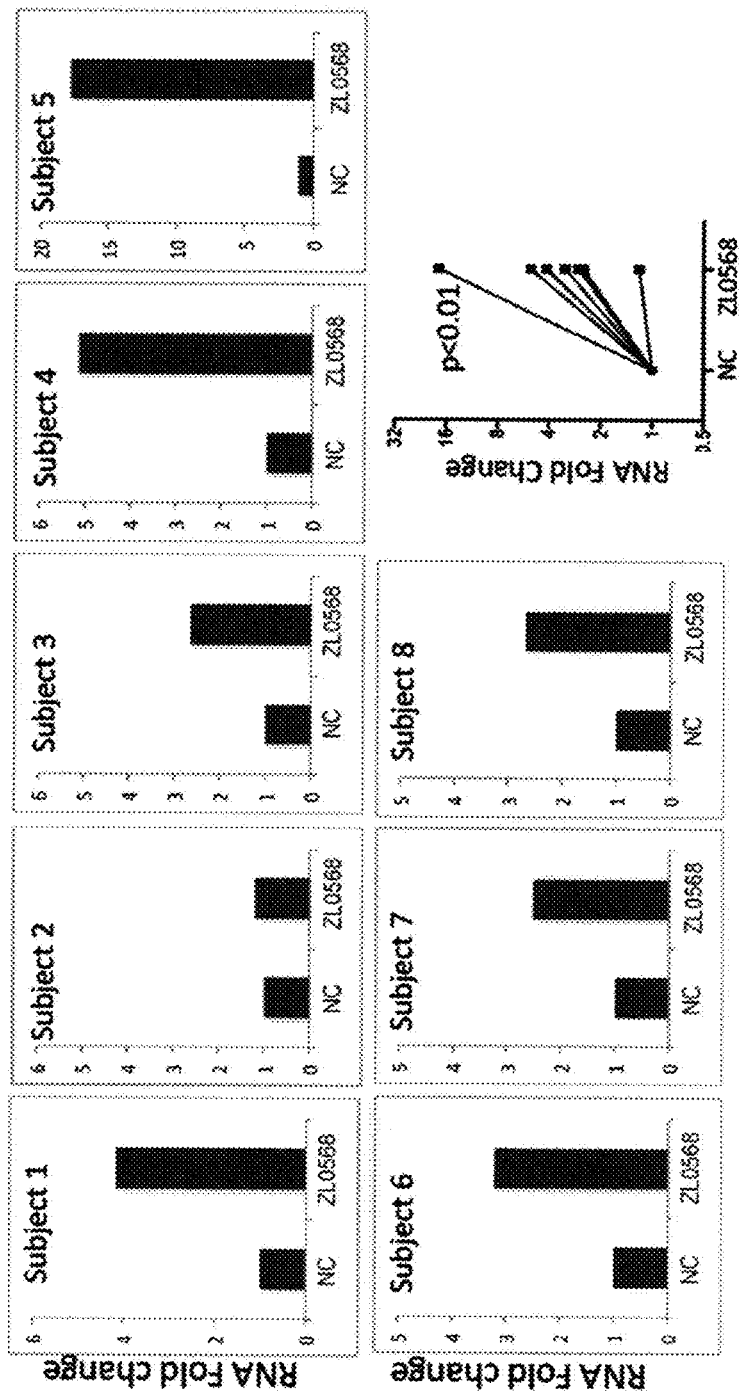
FIG. 6C. Relative HIV gene expression in multiple BMCs (n=8) after treatments were summarized.
Figure 6D:
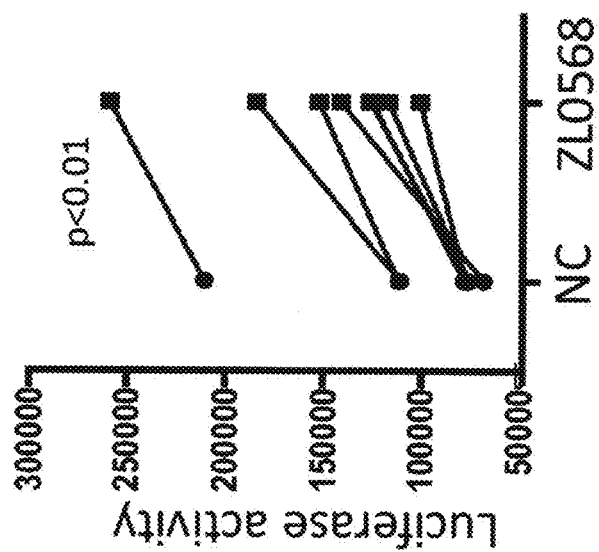
FIG. 6D. HIV release in supernatants of treated PBMC was measured by 1G5 reporter luciferase assay and compared between ZL0568 and NC.

Compound ZL0568 was further tested in multiple NNTC's donor PBMCs (n=8) for HIV gene activation (FIG. 6C) as well as viral production (FIG. 6D). Statistically significant results were observed for enhanced HIV activation by ZL0568 as compared to NC (p<0.01) (FIG. 6C-D). Taken together, these data provide strong evidence that compound ZL0568, an exemplary embodiment of the invention, can activate latent HIV in PBMC of ART-suppressed, aviremic HIV-infected subjects.

4.6. Specificity of ZL0568 in Activating Latent HIV in J-Lat: A Strong Structure-Activity Relationship (SAR).

Figure 7:
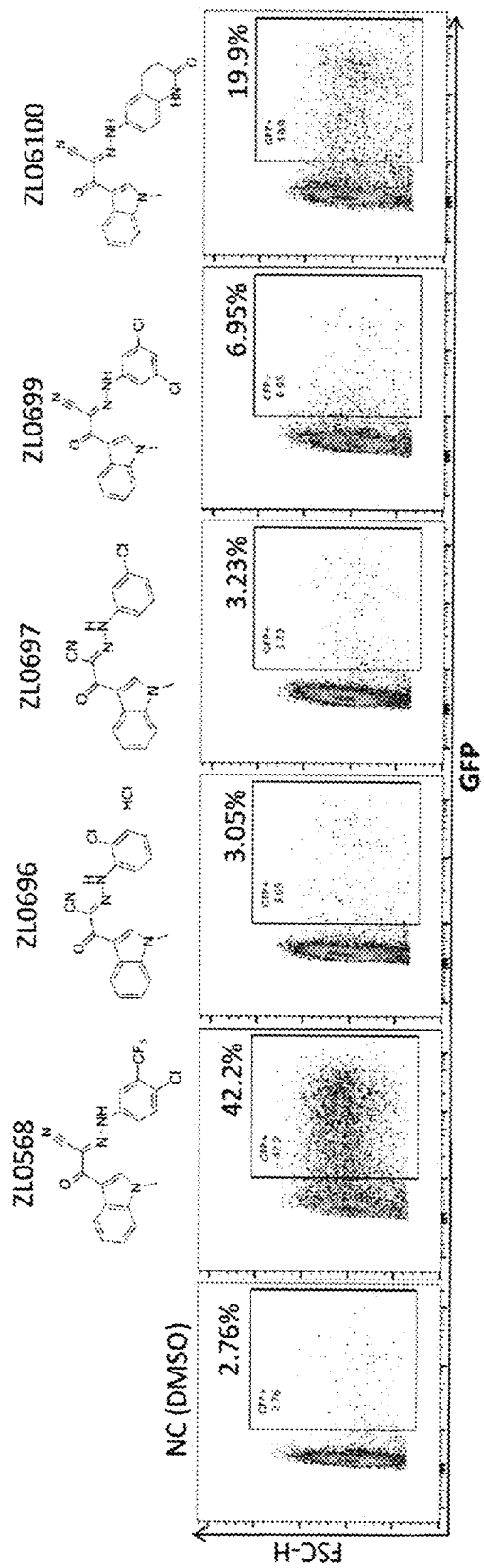
FIG. 7. Specificity and structure activity relationship (SAR) for ZL0568 compared with exemplary analogues (ZL0696, ZL0697, ZL0699 and ZL06100).

Specificity and structure-activity relationship (SAR) for ZL0568 was determined by synthesizing and testing four analogues (ZL0696, ZL0697, ZL0699 and ZL06100; 10 μM). Their structures compared to ZL0568 are shown in FIG. 7. It was found that modification of ZL0568 structure to its analogs substantially abrogated the ability to stimulate GFP expression in J-lat cells, except that the analog ZL06100 with 3,4-dihydroquinolin-2(1H)-one moiety still maintained some potency, but at lower level than ZL0568. These data strongly suggest the specificity of ZL0568 in activating latent HIV and a meaningful SAR for this class of molecules.

4.8. ZL0568 Shows Limited Cellular Toxicity and Induces Modest T-Cell Activation but No Production of Inflammatory Cytokines.

Figure 8B:
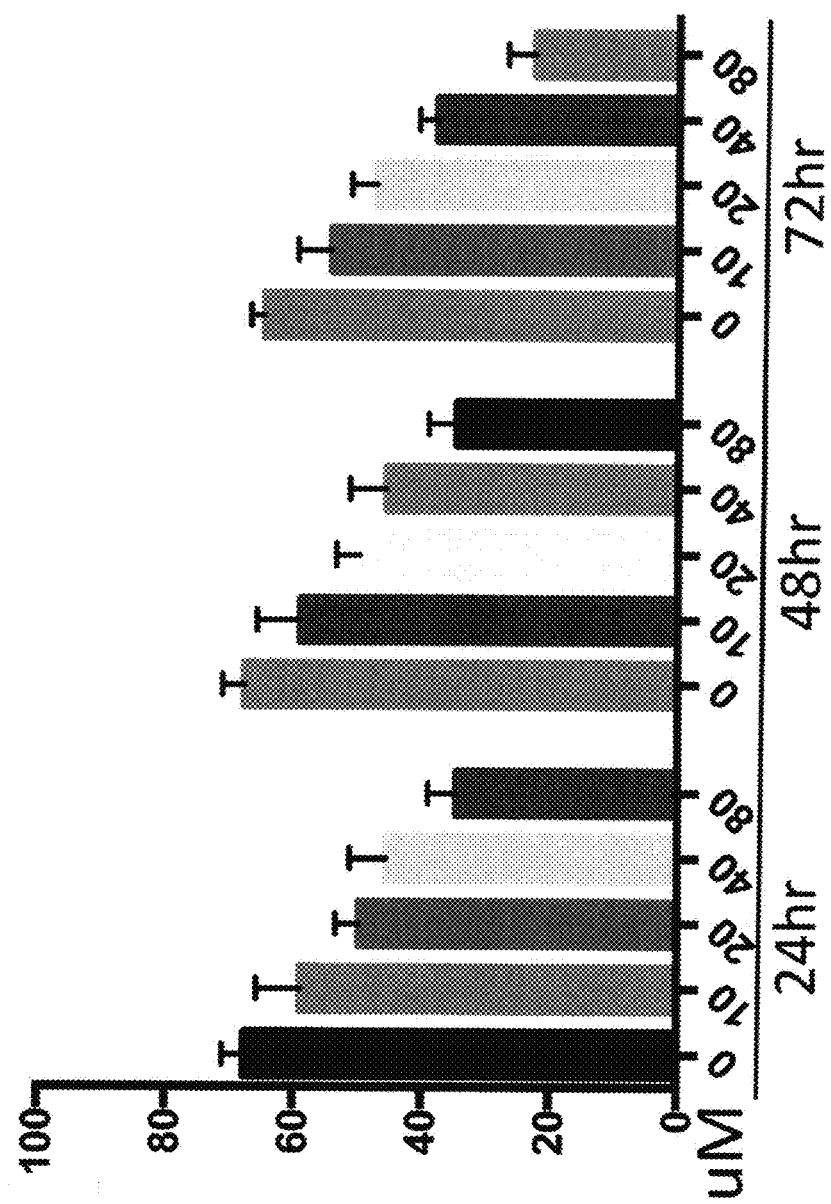
FIG. 8B. Cellular toxicity of ZL0568 on human PBMC. Toxicity was measured as % viable cells at Day 1, 2 and 3 after stimulation at various concentrations.
Figure 8C:
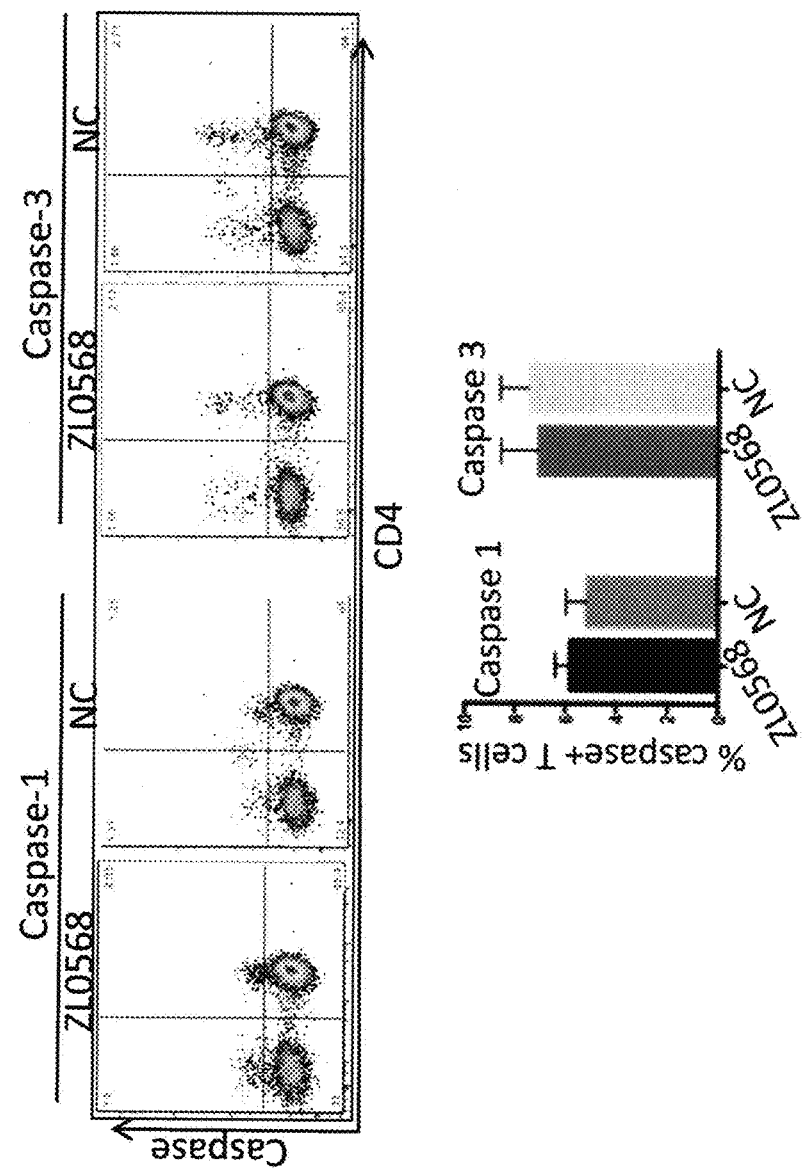
FIG. 8C. Caspase-3 and Caspase-1 expression in T cells with ZL0568 stimulation as compared to NC (24 hours).
Figure 8D:
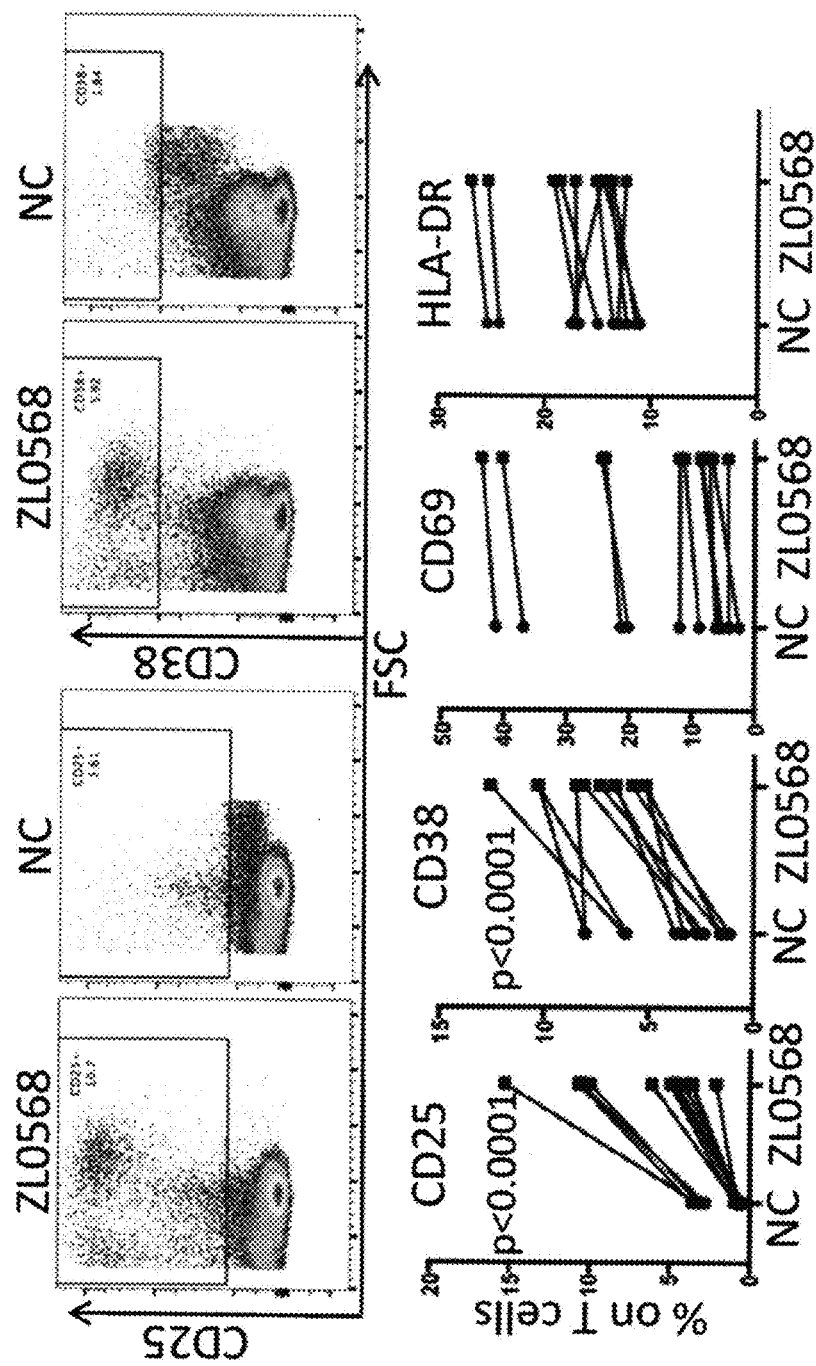
FIG. 8D. T-cell activation by ZL0568. Activation marker expression (CD25, CD38, CD69, HLA-DR) on T-cells was measured flow cytometry and compared between ZL0568 (10 uM) and NC.

Cellular toxicity profile of ZL0568 and its effects on human T cells was evaluated. It was found that even at a fairly high concentration (40 μM), ZL0568 caused limited cellular toxicity in both J-lat and human PBMC, which was measured as % viable cells (FIG. 8A-B) (cytotoxicity CC50=75 μM). It was also shown that there was no preferential induction of cell death signals (caspase-3/caspase-1) in T cells by ZL0568 treatment (FIG. 8C). This possibility was precluded since apoptosis was recently shown to be associated with HIV reactivation (68). Analysis of the effects of compound ZL0568 on T cells showed that ZL0568 (10 μM) caused modest T-cell activation, based on enhanced expression of CD25 and CD38 (p<0.001); no significant increase in CD69 and HLA-DR expression was observed (FIG. 8D). Critically, ZL0568 treatment did not induce expression of inflammatory cytokines in T cells (IFN-γ, IL-2, MIP-113 and IL-17) (FIG. 8E). This observation is intriguing, since recent study showed that only LRAs capable of activating T cells to some extent could reactivate latent HIV in primary cells (21). Overall, these data show that compound ZL0568 manifests a good cellular toxicity profile and induces modest T-cell activation but no production of cytokines.

4.9. Preparation of Exemplary Embodiments of the Invention

The general synthetic procedures and characterization data for certain embodiments of the invention as well as intermediates used in the preparation thereof is presented as follows:

1-Methyl-1H-indole (ZL0691)

To a solution of indole (3,510 mg, 30 mmol) in 100 mL THF at 0° C., NaH (3,600 mg, 90 mmol) was added. After 30 min at rt, the solution was cooled to 0° C. again, $CH_3I$ (4,260 mg, 30 mmol) was added dropwise. After 12 hours, the mixture was cooled to 0° C., saturated $NH_4Cl$ was added to quench the reaction. The mixture was extracted by EA twice. The combined organic layer was then washed with saturated $NaHCO_3$ and brine, dried over $Na_2SO_4$, filtrated and concentrated to give a light yellow liquid as a crude product.

3-(1-Methyl-1H-indol-3-yl)-3-oxopropanenitrile (ZL0693)

1-Methyl-1H-indole (1,000 mg, 7.63 mmol) was added to a solution prepared by dissolution of cyanoacetic acid (648 mg, 7.63 mmol) in 7 mL $Ac_2O$ at 50° C., and then the mixture was stirred at 85° C. for 10 min. After cooling to rt, the mixture was filtered to collect the white solid as desired product ZL0693 (1.02 g, 68% for two steps). $^1H$ NMR (300 MHz, DMSO) δ 8.38 (s, 1H), 8.15 (d, J=7.1 Hz, 1H), 7.59 (d, J=7.6 Hz, 1H), 7.31 (dq, J=13.3, 6.4 Hz, 2H), 4.45 (s, 2H), 3.89 (s, 3H).

(E)-N-(2-Chlorophenyl)-2-(1-methyl-1H-indol-3-yl)-2-oxoacetohydrazonoyl Cyanide (ZL0696)

To a solution of 2-chloroaniline (32 mg, 0.25 mmol) in 1 mL $H_2O$ and 1 mL $CH_3CN$, 10% HCl (0.92 mmol) was added at 0° C. After stirring at rt for 30 min, $NaNO_2$ (21 mg, 0.3 mmol) in 1 mL $H_2O$ was added. After stirring at 0° C. for 5 min, NaOAc (123 mg, 1.5 mmol) and ZL0693 (50 mg, 0.25 mmol) in 2 mL EtOH/DMF (1:1) were added. The mixture was filtered to give the desired product (84 mg, quant.) as a yellow solid. $^1$H NMR (300 MHz, DMSO) δ 15.32 (s, 1H), 10.50 (s, 1H), 8.68 (s, 1H), 8.47 (s, 1H), 8.33-8.23 (m, 1H), 7.80-7.54 (m, 3H), 7.48 (s, 1H), 7.41-7.19 (m, 3H), 3.95 (d, J=6.5 Hz, 3H). $^{13}$C NMR (75 MHz, DMSO) δ 180.22, 178.90, 139.44, 137.90, 137.50, 137.19, 130.48, 130.33, 129.32, 129.23, 127.39, 127.22, 126.86, 126.25, 124.52, 123.75, 123.06, 122.52, 121.97, 120.95, 119.41, 118.80, 116.55, 113.09, 112.89, 111.74, 111.34, 111.28, 34.22, 33.95.

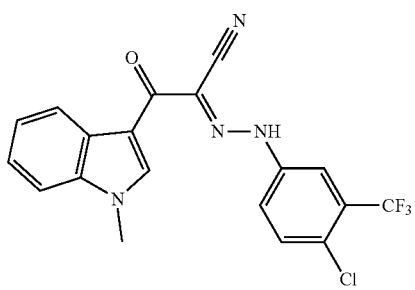

(E)-N-(4-chloro-3-(trifluoromethyl)phenyl)-2-(1-methyl-1H-indol-3-yl)-2-oxoacetohydrazonoyl Cyanide (ZL0568)

Yellow solid (99 mg, 98%). $^1$H NMR (300 MHz, DMSO) δ 12.22 (s, 1H), 8.48 (s, 1H), 8.24 (d, J=7.3 Hz, 1H), 7.95 (s, 1H), 7.75 (s, 2H), 7.60 (d, J=7.7 Hz, 1H), 7.36-7.25 (m, 2H), 3.93 (s, 3H). $^{13}$C NMR (75 MHz, DMSO) δ 179.47, 142.16, 139.65, 137.16, 133.24, 128.01, 127.60, 127.37, 125.15, 124.92, 123.71, 122.98, 121.87, 121.39, 116.95, 115.90, 115.82, 111.75, 111.43, 111.28, 33.76.

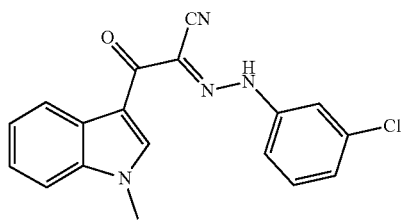

(E)-N-(3-Chlorophenyl)-2-(1-methyl-1H-indol-3-yl)-2-oxoacetohydrazonoyl Cyanide (ZL0697)

Yellow solid (83 mg, 99%). $^1$H NMR (300 MHz, DMSO) δ 12.01 (s, 1H), 8.42 (s, 1H), 8.24 (d, J=7.7 Hz, 1H), 7.59 (d, J=7.8 Hz, 1H), 7.53 (s, 1H), 7.45 (d, J=5.8 Hz, 2H), 7.36-7.24 (m, 2H), 7.21-7.15 (m, 1H), 3.93 (s, 3H). $^{13}$C NMR (75 MHz, DMSO) δ 179.67, 144.26, 139.47, 137.16, 134.37, 131.67, 127.40, 124.15, 123.65, 122.90, 121.91, 116.51, 116.26, 115.22, 111.90, 111.54, 111.24, 33.84.

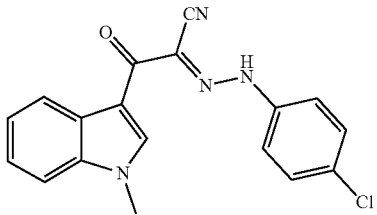

(E)-N-(4-Chlorophenyl)-2-(1-methyl-1H-indol-3-yl)-2-oxoacetohydrazonoyl Cyanide (ZL0698)

Yellow solid (79 mg, 94%). $^1$H NMR (300 MHz, DMSO) δ 12.01 (s, 1H), 8.40 (s, 1H), 8.26 (d, J=7.5 Hz, 1H), 7.59 (d, J=7.8 Hz, 1H), 7.50 (q, J=8.9 Hz, 4H), 7.31 (dd, J=15.6, 7.4 Hz, 2H), 3.94 (s, 3H). $^{13}$C NMR (75 MHz, DMSO) δ 179.73, 141.81, 139.29, 137.14, 129.85, 128.54, 127.45, 123.62, 122.86, 121.96, 118.39, 115.88, 112.04, 111.59, 111.20, 33.89.

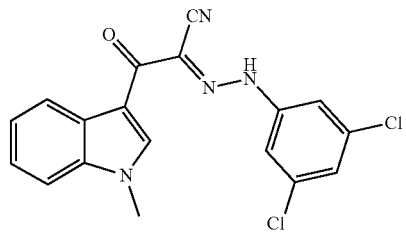

(E)-N-(3,5-Dichlorophenyl)-2-(1-methyl-1H-indol-3-yl)-2-oxoacetohydrazonoyl Cyanide (ZL0699)

Yellow solid (40 mg, 43%). $^1$H NMR (300 MHz, DMSO) δ 12.08 (s, 1H), 8.45 (s, 1H), 8.22 (d, J=7.4 Hz, 1H), 7.59 (d, J=7.9 Hz, 1H), 7.46 (s, 2H), 7.37-7.25 (m, 3H), 3.93 (s, 3H). $^{13}$C NMR (75 MHz, DMSO) δ 179.43, 145.13, 139.82, 137.22, 135.30, 127.31, 123.72, 123.34, 122.99, 121.85, 117.19, 115.22, 111.66, 111.48, 111.31, 33.79.

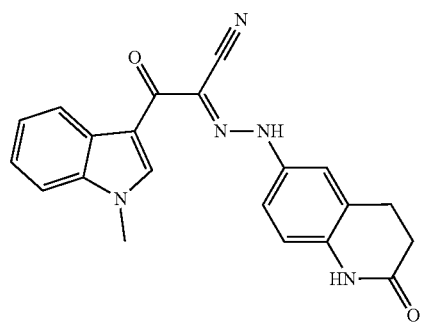

(E)-2-(1-Methyl-1H-indol-3-yl)-2-oxo-N-(2-oxo-1,2,3,4-tetrahydroquinolin-6-yl)acetohydrazonoyl Cyanide (ZL06100)

Yellow solid (76 mg, 82%). $^1$H NMR (300 MHz, DMSO) δ 11.91 (s, 1H), 10.14 (s, 1H), 8.41 (s, 1H), 8.26 (d, J=7.8

Hz, 1H), 7.58 (d, J=7.8 Hz, 1H), 7.31 (dd, J=17.9, 9.5 Hz, 4H), 6.91 (d, J=8.4 Hz, 1H), 3.94 (s, 3H), 2.93 (t, J=7.5 Hz, 2H), 2.46 (d, J=7.1 Hz, 2H). $^{13}$C NMR (75 MHz, DMSO) δ 180.00, 170.39, 138.95, 137.52, 137.05, 135.76, 127.51, 125.34, 123.49, 122.70, 122.00, 116.52, 116.29, 115.94, 114.30, 112.43, 111.64, 111.11, 33.83, 30.71, 25.57.

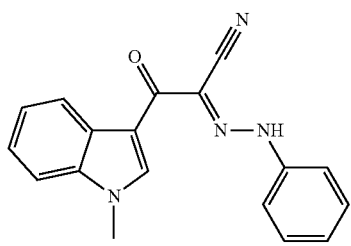

ZL0701

(E)-2-(1-Methyl-1H-indol-3-yl)-2-oxo-N-phenylacetohydrazonoyl Cyanide (ZL0701)

Yellow solid (60 mg, 80%). $^1$H NMR (300 MHz, DMSO) δ 11.94 (s, 1H), 8.42 (s, 1H), 8.27 (d, J=7.5 Hz, 1H), 7.59 (d, J=7.8 Hz, 1H), 7.53 (d, J=8.1 Hz, 2H), 7.44 (t, J=7.8 Hz, 2H), 7.36-7.25 (m, 2H), 7.16 (t, J=7.1 Hz, 1H), 3.94 (s, 3H). $^{13}$C NMR (75 MHz, DMSO) δ 179.91, 142.77, 139.17, 137.12, 130.00, 127.48, 124.78, 123.59, 122.83, 121.98, 116.77, 115.31, 112.15, 111.61, 111.19, 33.89.

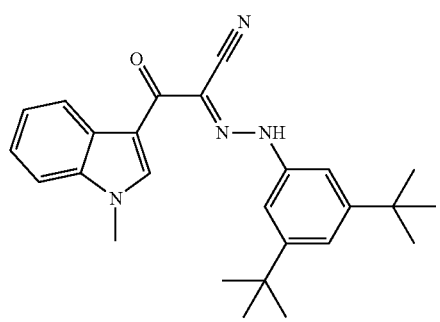

ZL0702

(E)-N-(3,5-Di-tert-butylphenyl)-2-(1-methyl-1H-indol-3-yl)-2-oxoacetohydrazonoyl Cyanide (ZL0702)

Yellow solid (88 mg, 85%). $^1$H NMR (300 MHz, DMSO) δ 11.95 (s, 1H), 8.47 (s, 1H), 8.27 (d, J=7.5 Hz, 1H), 7.59 (d, J=7.7 Hz, 1H), 7.42 (s, 2H), 7.30 (dt, J=14.8, 7.2 Hz, 2H), 7.24 (d, J=6.4 Hz, 1H), 3.90 (s, 3H), 1.32 (s, 18H). $^{13}$C NMR (75 MHz, DMSO) δ 180.11, 152.25, 142.35, 138.87, 137.02, 127.51, 123.54, 122.78, 121.99, 118.96, 114.42, 112.23, 111.75, 111.26, 111.15, 35.18, 33.75, 31.59.

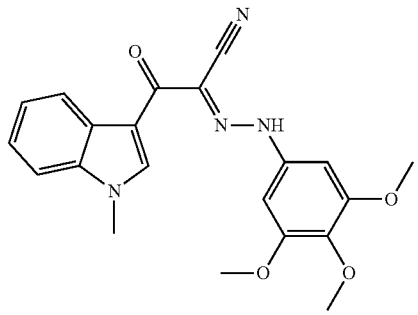

ZL0703

(E)-2-(1-Methyl-1H-indol-3-yl)-2-oxo-N-(3,4,5-trimethoxyphenyl)acetohydrazonoyl Cyanide (ZL0703)

Yellow solid (92 mg, 94%). $^1$H NMR (300 MHz, DMSO) δ 11.90 (s, 1H), 8.50 (s, 1H), 8.25 (d, J=7.5 Hz, 1H), 7.58 (d, J=7.8 Hz, 1H), 7.36-7.21 (m, 2H), 6.88 (s, 2H), 3.91 (s, 3H), 3.83 (s, 6H), 3.66 (s, 3H). $^{13}$C NMR (75 MHz, DMSO) δ 179.93, 153.99, 138.95, 138.81, 137.08, 134.81, 127.47, 123.53, 122.77, 121.95, 114.63, 112.19, 111.59, 111.16, 94.30, 60.65, 56.12, 33.65.

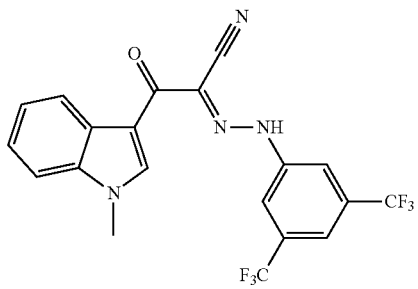

ZL0704

(E)-N-(3,5-Bis(trifluoromethyl)phenyl)-2-(1-methyl-1H-indol-3-yl)-2-oxoacetohydrazonoyl Cyanide (ZL0704)

Yellow solid (72 mg, 66%). $^1$H NMR (300 MHz, DMSO) δ 12.37 (s, 1H), 8.54 (s, 1H), 8.22 (d, J=7.6 Hz, 1H), 8.05 (s, 2H), 7.82 (s, 1H), 7.60 (d, J=7.5 Hz, 1H), 7.40-7.21 (m, 2H), 3.90 (s, 3H). $^{13}$C NMR (75 MHz, DMSO) δ 179.36, 144.62, 140.01, 137.18, 132.05, 131.61, 127.30, 123.76, 123.03, 121.80, 117.65, 116.82, 111.52, 111.40, 111.33, 33.61.

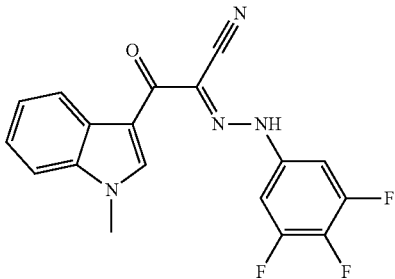

ZL0705

(E)-2-(1-Methyl-1H-indol-3-yl)-2-oxo-N-(3,4,5-trifluorophenyl)acetohydrazonoyl Cyanide (ZL0705)

Yellow solid (94 mg, quant.). $^1$H NMR (300 MHz, DMSO) δ 12.03 (s, 1H), 8.42 (s, 1H), 8.23 (d, J=7.7 Hz, 1H), 7.58 (d, J=7.7 Hz, 1H), 7.31 (dd, J=15.5, 7.1 Hz, 4H), 3.93 (s, 3H). $^{13}$C NMR (75 MHz, DMSO) δ 179.31, 149.50, 139.69, 137.23, 127.35, 123.69, 122.95, 121.90, 117.18, 111.77, 111.44, 111.25, 101.50, 101.18, 33.84.

130.85, 127.48, 123.56, 122.80, 121.97, 115.19, 112.20, 111.66, 111.18, 111.09, 109.11, 101.85, 55.51, 33.80.

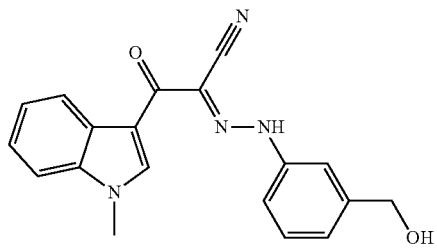

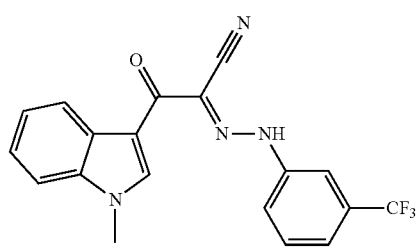

(E)-2-(1-Methyl-1H-indol-3-yl)-2-oxo-N-(3-(trifluoromethyl)phenyl)acetohydrazonoyl Cyanide (ZL0706)

Yellow solid (86 mg, 93%). $^1$H NMR (300 MHz, DMSO) δ 12.17 (s, 1H), 8.46 (s, 1H), 8.25 (d, J=7.1 Hz, 1H), 7.82 (s, 1H), 7.78 (d, J=8.3 Hz, 1H), 7.67 (t, J=7.9 Hz, 1H), 7.60 (d, J=7.7 Hz, 1H), 7.48 (d, J=7.6 Hz, 1H), 7.36-7.25 (m, 2H), 3.92 (s, 3H). $^{13}$C NMR (75 MHz, DMSO) δ 179.64, 143.54, 139.56, 137.15, 131.27, 130.82, 130.39, 127.39, 123.67, 122.93, 121.89, 120.72, 120.67, 120.27, 116.49, 113.25, 113.20, 113.14, 113.09, 111.82, 111.50, 111.25, 33.75.

(E)-N-(3-(Hydroxymethyl)phenyl)-2-(1-methyl-1H-indol-3-yl)-2-oxoacetohydrazonoyl Cyanide (ZL0708)

Yellow solid (74 mg, 89%). $^1$H NMR (300 MHz, DMSO) δ 12.00 (s, 1H), 8.45 (s, 1H), 8.31-8.23 (m, 1H), 7.59 (d, J=7.3 Hz, 2H), 7.39 (t, J=7.2 Hz, 2H), 7.31 (ddd, J=15.1, 9.7, 4.2 Hz, 2H), 7.08 (d, J=6.2 Hz, 1H), 5.34 (t, J=5.5 Hz, 1H), 4.57 (d, J=5.2 Hz, 2H), 3.94 (s, 3H). $^{13}$C NMR (75 MHz, DMSO) δ 179.94, 144.80, 142.82, 139.11, 137.04, 129.62, 127.52, 123.57, 122.81, 122.58, 121.97, 115.25, 115.02, 114.24, 112.11, 111.53, 111.16, 63.06, 33.82.

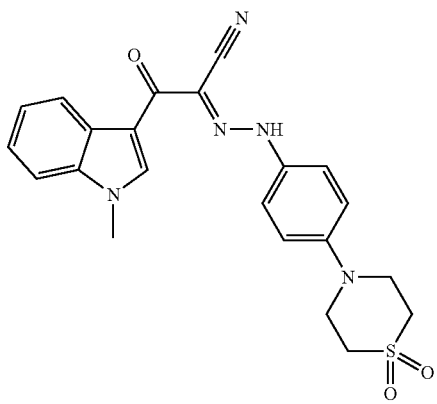

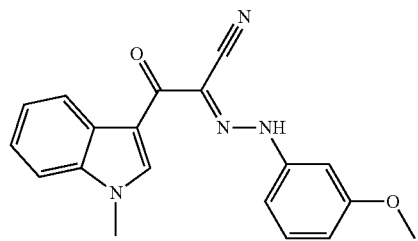

(E)-N-(3-Methoxyphenyl)-2-(1-methyl-1H-indol-3-yl)-2-oxoacetohydrazonoyl Cyanide (ZL0707)

Orange solid (80 mg, 96%). $^1$H NMR (300 MHz, DMSO) δ 11.93 (s, 1H), 8.44 (s, 1H), 8.26 (d, J=7.4 Hz, 1H), 7.58 (d, J=7.7 Hz, 1H), 7.36-7.23 (m, 3H), 7.15-7.07 (m, 2H), 6.73 (d, J=8.2 Hz, 1H), 3.92 (s, 3H), 3.80 (s, 3H). $^{13}$C NMR (75 MHz, DMSO) δ 179.92, 160.68, 144.23, 139.07, 137.11,

(E)-N-(4-(1,1-Dioxidothiomorpholino)phenyl)-2-(1-methyl-1H-indol-3-yl)-2-oxoacetohydrazonoyl Cyanide (ZL0710)

Yellow solid (96 mg, 88%). $^1$H NMR (300 MHz, DMSO) δ 11.88 (s, 1H), 8.38 (s, 1H), 8.27 (d, J=7.4 Hz, 1H), 7.58 (d, J=7.8 Hz, 1H), 7.45 (d, J=8.9 Hz, 2H), 7.35-7.23 (m, 2H), 7.12 (d, J=8.9 Hz, 2H), 3.93 (s, 3H), 3.78 (s, 4H), 3.14 (s, 4H). $^{13}$C NMR (75 MHz, DMSO) δ 180.06, 145.37, 138.73, 137.03, 135.44, 127.52, 123.49, 122.70, 122.02, 118.20, 117.31, 113.91, 112.56, 111.74, 111.11, 50.33, 47.51, 33.85.

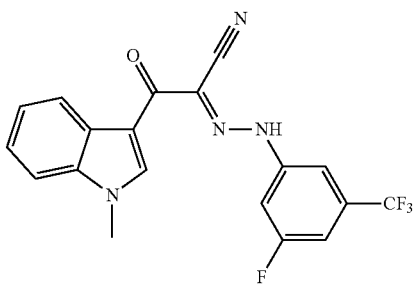

(E)-N-(3-Fluoro-5-(trifluoromethyl)phenyl)-2-(1-methyl-1H-indol-3-yl)-2-oxoacetohydrazonoyl Cyanide (ZL0711)

Yellow solid (79 mg, 81%). $^1$H NMR (300 MHz, DMSO) δ 12.21 (s, 1H), 8.46 (s, 1H), 8.23 (d, J=7.4 Hz, 1H), 7.66 (s, 1H), 7.59 (d, J=7.8 Hz, 1H), 7.52 (d, J=10.5 Hz, 1H), 7.39 (d, J=8.5 Hz, 1H), 7.32 (dd, J=15.9, 7.3 Hz, 2H), 3.91 (s, 3H). $^{13}$C NMR (75 MHz, DMSO) δ 179.35, 164.78, 161.53, 145.59, 145.44, 139.83, 137.20, 127.32, 123.74, 123.01, 121.85, 117.42, 111.60, 111.42, 111.29, 109.43, 108.06, 107.54, 107.19, 33.72.

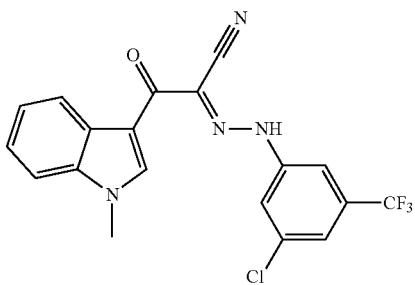

(E)-N-(3-Chloro-5-(trifluoromethyl)phenyl)-2-(1-methyl-1H-indol-3-yl)-2-oxoacetohydrazonoyl Cyanide (ZL0712)

Yellow solid (79 mg, 78%). $^1$H NMR (300 MHz, DMSO) δ 12.21 (s, 1H), 8.47 (s, 1H), 8.22 (d, J=7.3 Hz, 1H), 7.73 (s, 2H), 7.62-7.52 (m, 2H), 7.37-7.23 (m, 2H), 3.90 (s, 3H). $^{13}$C NMR (75 MHz, DMSO) δ 179.37, 144.96, 139.85, 137.18, 135.48, 132.32, 131.89, 127.30, 123.73, 122.99, 121.83, 120.21, 120.16, 119.90, 117.41, 111.88, 111.58, 111.43, 111.29, 33.68.

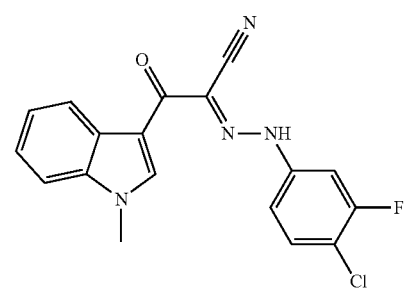

(E)-N-(4-Chloro-3-fluorophenyl)-2-(1-methyl-1H-indol-3-yl)-2-oxoacetohydrazonoyl Cyanide (ZL0713)

Yellow solid (84 mg, 95%). $^1$H NMR (300 MHz, DMSO) δ 12.07 (s, 1H), 8.41 (s, 1H), 8.24 (d, J=7.0 Hz, 1H), 7.61 (dd, J=11.9, 8.2 Hz, 2H), 7.44 (d, J=11.1 Hz, 1H), 7.38-7.24 (m, 3H), 3.93 (s, 3H). $^{13}$C NMR (75 MHz, DMSO) δ 179.48, 159.66, 156.41, 143.43, 143.30, 139.56, 137.20, 131.80, 127.38, 123.69, 122.95, 121.92, 116.75, 114.59, 114.35, 113.70, 111.83, 111.49, 111.25, 105.43, 105.08, 33.87.

(E)-N-(3,4-Dichlorophenyl)-2-(1-methyl-1H-indol-3-yl)-2-oxoacetohydrazonoyl Cyanide (ZL0714)

Yellow solid (87 mg, 94%). $^1$H NMR (300 MHz, DMSO) δ 12.06 (s, 1H), 8.41 (s, 1H), 8.23 (d, J=7.1 Hz, 1H), 7.69-7.63 (m, 2H), 7.59 (d, J=7.5 Hz, 1H), 7.46 (dd, J=8.8, 2.5 Hz, 1H), 7.36-7.24 (m, 2H), 3.93 (s, 3H). $^{13}$C NMR (75 MHz, DMSO) δ 179.53, 142.92, 139.56, 137.17, 132.27, 131.83, 127.37, 126.11, 123.68, 122.94, 121.90, 118.32, 116.78, 116.69, 111.84, 111.51, 111.25, 33.84.

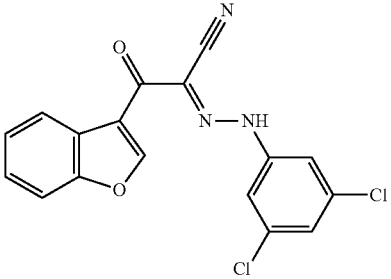

(E)-2-(benzofuran-3-yl)-N-(3,5-dichlorophenyl)-2-oxoacetohydrazonoyl Cyanide (ZL0570)

Yellow solid (94 mg, quant.). $^1$H NMR (300 MHz, DMSO) δ 7.93 (s, 1H), 7.86 (d, J=7.8 Hz, 1H), 7.72 (d, J=8.4 Hz, 1H), 7.57 (t, J=7.7 Hz, 1H), 7.51 (d, J=1.6 Hz, 2H), 7.38 (dd, J=12.1, 4.5 Hz, 2H). $^{13}$C NMR (75 MHz, DMSO) δ 174.88, 155.47, 150.18, 145.00, 135.40, 129.16, 127.15, 124.64, 124.34, 124.26, 117.58, 115.74, 115.12, 112.41, 111.04.

3-(1H-indol-3-yl)-3-oxopropanenitrile (ZL0743)

Indole (2,340 mg, 20 mmol) was added to a solution prepared by dissolution of cyanoacetic acid (2,040 mg, 24 mmol) in 20 mL Ac$_2$O at 50° C., and then the mixture was stirred at 85° C. for 10 min. After cooling to rt, the mixture was filtered to collect the white solid as desired product ZL0743 (3.17 g, 86%). The product was put into next step directly.

(E)-N-(4-chloro-3-(trifluoromethyl)phenyl)-2-(1H-indol-3-yl)-2-oxoacetohydrazonoyl Cyanide (ZL0744)

To a solution of 4-chloro-3-(trifluoromethyl)aniline (49 mg, 0.25 mmol) in 1 mL H$_2$O and 1 mL CH$_3$CN, 10% HCl (1.0 mmol) was added at 0° C. After stirring at rt for 30 min, NaNO$_2$ (21 mg, 0.3 mmol) in 1 mL H$_2$O was added. After stirring at 0° C. for 5 min, NaOAc (123 mg, 1.5 mmol) and ZL0743 (46 mg, 0.25 mmol) in 2 mL EtOH/DMF (1:1) were added. The mixture was filtered to give the desired product (81 mg, 84%) as a yellow solid. $^1$H NMR (300 MHz, DMSO) δ 12.18 (s, 2H), 8.46 (d, J=2.6 Hz, 1H), 8.23 (d, J=7.7 Hz, 1H), 7.95 (s, 1H), 7.74 (d, J=9.0 Hz, 2H), 7.53 (d, J=6.9 Hz, 1H), 7.30-7.19 (m, 2H). $^{13}$C NMR (75 MHz, DMSO) δ 179.97, 142.25, 136.51, 136.13, 133.19, 128.06, 127.65, 126.92, 125.13, 123.64, 122.60, 121.76, 121.18, 117.17, 115.90, 115.75, 115.68, 112.79, 112.66, 111.80.

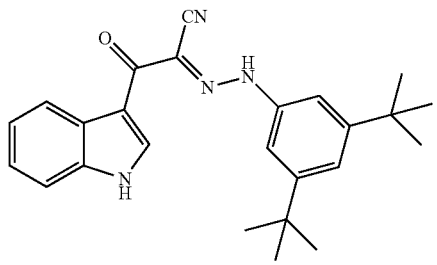

ZL0745

(E)-N-(3,5-di-tert-butylphenyl)-2-(1H-indol-3-yl)-2-oxoacetohydrazonoyl Cyanide (ZL0745)

ZL0745 (79 mg, 79%) was obtained as a yellow solid following the procedure of ZL0744. $^1$H NMR (300 MHz, DMSO) δ 12.24 (s, 1H), 11.94 (s, 1H), 8.45 (d, J=3.0 Hz, 1H), 8.26 (dd, J=6.1, 2.6 Hz, 1H), 7.54 (dd, J=6.1, 2.4 Hz, 1H), 7.40 (d, J=1.4 Hz, 2H), 7.31-7.18 (m, 3H), 1.31 (s, 18H). $^{13}$C NMR (75 MHz, DMSO) δ 180.55, 152.27, 142.33, 136.39, 135.18, 127.05, 123.44, 122.42, 121.86, 118.91, 114.53, 112.83, 112.71, 112.23, 111.17, 35.19, 31.65.

1-Benzyl-1H-indole (ZL0747)

To a solution of indole (936 mg, 8 mmol) in 10 mL DMF at 0° C., NaH (320 mg, 24 mmol) was added. After 30 min at rt, the solution was cooled to 0° C. again, BnBr (1,368 mg, 8 mmol) was added dropwise. After 12 hours, the mixture was cooled to 0° C., saturated NH$_4$Cl was added to quench the reaction. The mixture was extracted by EA twice. The combined organic layer was then washed with saturated NaHCO$_3$ and brine, dried over Na$_2$SO$_4$, filtrated and concentrated to give a light yellow liquid as a crude product.

3-(1-Benzyl-1H-indol-3-yl)-3-oxopropanenitrile (ZL0752)

1-Benzyl-1H-indole (8 mmol) was added to a solution prepared by dissolution of cyanoacetic acid (1056 mg, 8 mmol) in 7 mL Ac$_2$O at 50° C., and then the mixture was stirred at 85° C. for 10 min. After cooling to rt, the mixture was filtered to collect the yellow solid as desired product ZL0752 (1.47 g, 67% for two steps). The product was put into next step directly.

(E)-2-(1-benzyl-1H-indol-3-yl)-N-(4-chloro-3-(trifluoromethyl)phenyl)-2-oxoacetohydrazonoyl Cyanide (ZL0755)

To a solution of 4-chloro-3-(trifluoromethyl)aniline (49 mg, 0.25 mmol) in 1 mL H$_2$O and 1 mL CH$_3$CN, 10% HCl (0.92 mmol) was added at 0° C. After stirring at rt for 30 min, NaNO$_2$ (21 mg, 0.3 mmol) in 1 mL H$_2$O was added. After stirring at 0° C. for 5 min, NaOAc (123 mg, 1.5 mmol) and ZL0755 (50 mg, 0.25 mmol) in 2 mL EtOH/DMF (1:1) were added. The mixture was filtered to give the desired product (88 mg, 73%) as a yellow solid. $^1$H NMR (300 MHz, DMSO) δ 12.23 (s, 1H), 8.63 (s, 1H), 8.29-8.21 (m, 1H), 7.97 (s, 1H), 7.68-7.56 (m, 3H), 7.30 (dd, J=21.2, 7.3 Hz, 7H), 5.58 (s, 2H). $^{13}$C NMR (75 MHz, DMSO) δ 179.74, 142.22, 139.07, 137.21, 136.52, 133.07, 129.18, 128.27, 127.81, 127.60, 125.16, 123.83, 123.05, 122.05, 121.19, 117.05, 116.22, 116.15, 116.07, 115.99, 112.06, 111.75, 50.31.

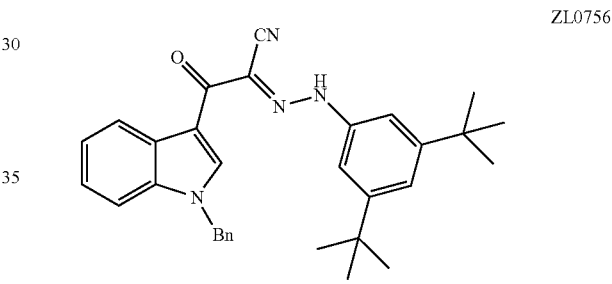

ZL0756

(E)-2-(1-benzyl-1H-indol-3-yl)-N-(3,5-di-tert-butylphenyl)-2-oxoacetohydrazonoyl Cyanide (ZL0756)

ZL0756 (106 mg, 87%) was obtained as a yellow solid following the procedure of ZL0755. $^1$H NMR (300 MHz, DMSO) δ 11.95 (s, 1H), 8.71 (s, 1H), 8.36-8.23 (m, 1H), 7.47-7.42 (m, 1H), 7.40 (d, J=1.5 Hz, 2H), 7.33-7.22 (m, 5H), 7.18 (d, J=6.9 Hz, 3H), 5.59 (s, 2H), 1.24 (s, 18H). $^{13}$C NMR (75 MHz, DMSO) δ 180.29, 152.17, 142.26, 138.67, 137.24, 136.33, 129.13, 128.03, 127.88, 126.99, 123.68, 122.88, 122.28, 118.96, 114.66, 112.36, 112.29, 111.76, 111.35, 50.47, 35.10, 31.54.

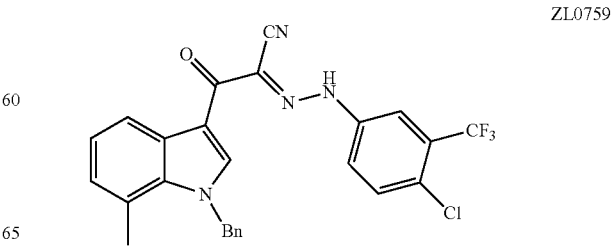

ZL0759

(E)-N-(4-chloro-3-(trifluoromethyl)phenyl)-2-(1,7-dimethyl-1H-indol-3-yl)-2-oxoacetohydrazonoyl Cyanide (ZL0759)

Yellow solid (49 mg, 47%). ¹H NMR (300 MHz, DMSO) δ 12.17 (s, 1H), 8.36 (s, 1H), 8.10 (d, J=7.8 Hz, 1H), 7.93 (s, 1H), 7.73 (s, 2H), 7.11 (t, J=7.5 Hz, 1H), 7.00 (d, J=7.1 Hz, 1H), 4.16 (s, 3H), 2.76 (s, 3H). ¹³C NMR (75 MHz, DMSO) δ 179.30, 142.16, 141.14, 135.78, 133.20, 128.52, 126.29, 125.09, 123.09, 122.87, 121.36, 119.91, 117.05, 115.83, 111.75, 110.88, 37.80, 19.42.

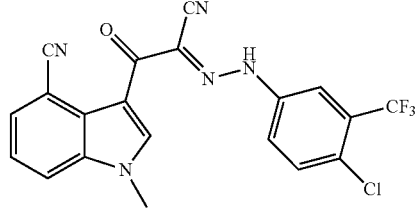

(E)-N-(3,5-di-tert-butylphenyl)-2-(1,7-dimethyl-1H-indol-3-yl)-2-oxoacetohydrazonoyl Cyanide (ZL0760)

Yellow solid (35 mg, 33%). ¹H NMR (300 MHz, DMSO) δ 11.92 (s, 1H), 8.36 (s, 1H), 8.14 (d, J=7.8 Hz, 1H), 7.41 (s, 2H), 7.22 (s, 1H), 7.10 (t, J=7.6 Hz, 1H), 7.00 (d, J=7.0 Hz, 1H), 4.15 (s, 3H), 2.76 (s, 3H), 1.32 (s, 18H). ¹³C NMR (75 MHz, DMSO) δ 180.00, 152.19, 142.64, 140.36, 135.63, 128.69, 126.10, 122.85, 122.70, 120.04, 118.87, 114.46, 111.30, 37.82, 35.18, 31.62, 19.47.

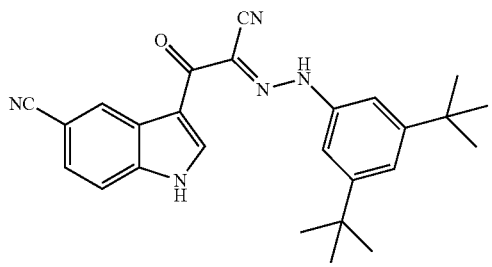

(E)-2-(5-cyano-1H-indol-3-yl)-N-(3,5-di-tert-butylphenyl)-2-oxoacetohydrazonoyl Cyanide (ZL0762)

Yellow solid (63 mg, 59%). ¹H NMR (300 MHz, DMSO) δ 12.70 (s, 1H), 12.10 (s, 1H), 8.64-8.54 (m, 2H), 7.72 (d, J=8.4 Hz, 1H), 7.62 (dd, J=8.5, 1.3 Hz, 1H), 7.39 (d, J=1.3 Hz, 2H), 7.23 (s, 1H), 1.30 (s, 18H). ¹³C NMR (75 MHz, DMSO) δ 180.67, 152.29, 142.16, 138.26, 137.14, 126.95, 126.80, 126.27, 120.62, 119.27, 114.24, 114.09, 113.18, 112.01, 111.36, 104.61, 35.19, 31.61.

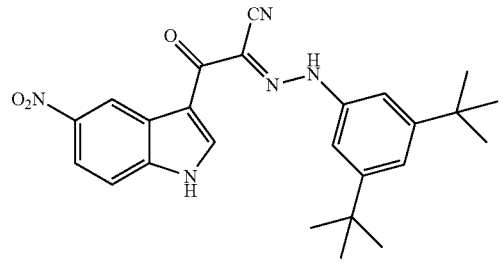

(E)-N-(3,5-di-tert-butylphenyl)-2-(5-nitro-1H-indol-3-yl)-2-oxoacetohydrazonoyl Cyanide (ZL0769)

Yellow solid (33 mg, 30%). ¹H NMR (300 MHz, DMSO) δ 12.82 (s, 1H), 12.15 (s, 1H), 9.12 (d, J=2.2 Hz, 1H), 9.04 (d, J=2.3 Hz, 1H), 8.64 (d, J=2.7 Hz, 1H), 8.15 (dd, J=9.0, 2.3 Hz, 1H), 7.73 (d, J=9.0 Hz, 1H), 7.40 (d, J=1.3 Hz, 2H), 7.25 (s, 1H), 1.31 (s, 18H).

(E)-N-(4-chloro-3-(trifluoromethyl)phenyl)-2-(4-cyano-1-methyl-1H-indol-3-yl)-2-oxoacetohydrazonoyl Cyanide (ZL0770)

Yellow solid (71 mg, 66%). ¹H NMR (300 MHz, DMSO) δ 12.42 (s, 1H), 8.55 (s, 1H), 8.00 (d, J=8.2 Hz, 1H), 7.83 (d, J=2.2 Hz, 1H), 7.77-7.62 (m, 3H), 7.47 (t, J=7.9 Hz, 1H), 3.98 (s, 3H). ¹³C NMR (75 MHz, DMSO) δ 179.72, 142.00, 141.01, 137.82, 133.19, 130.06, 128.42, 128.00, 127.59, 127.18, 125.53, 124.80, 123.44, 121.46, 121.18, 118.83, 116.92, 116.23, 115.87, 115.79, 115.72, 115.64, 111.80, 111.63, 103.72, 33.94.

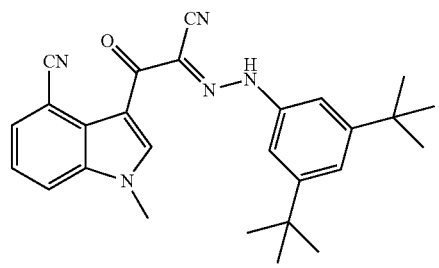

(E)-2-(4-cyano-1-methyl-1H-indol-3-yl)-N-(3,5-di-tert-butylphenyl)-2-oxoacetohydrazonoyl Cyanide (ZL0772)

Yellow solid (79 mg, 72%). ¹H NMR (300 MHz, DMSO) δ 12.17 (s, 1H), 8.49 (s, 1H), 7.99 (d, J=8.3 Hz, 1H), 7.72

(d, J=7.4 Hz, 1H), 7.46 (t, J=7.9 Hz, 1H), 7.29 (d, J=1.4 Hz, 2H), 7.19 (s, 1H), 3.96 (s, 3H), 1.23 (s, 18H). $^{13}$C NMR (75 MHz, DMSO) δ 180.60, 152.15, 142.32, 140.00, 137.65, 129.77, 125.68, 123.14, 119.21, 118.91, 116.77, 113.70, 112.44, 112.20, 111.21, 103.76, 35.10, 33.92, 31.51.

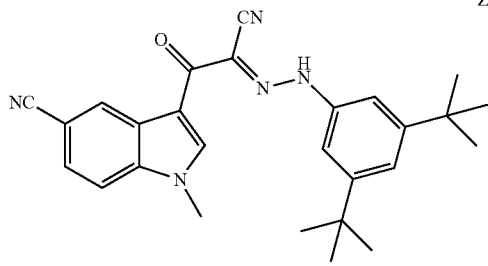

ZL0774

(E)-2-(5-cyano-1-methyl-1H-indol-3-yl)-N-(3,5-di-tert-butylphenyl)-2-oxoacetohydrazonoyl Cyanide (ZL0774)

Yellow solid (32 mg, 30%). $^1$H NMR (300 MHz, DMSO) δ 12.11 (s, 1H), 8.61 (d, J=4.5 Hz, 2H), 7.81 (d, J=8.5 Hz, 1H), 7.70 (d, J=8.6 Hz, 1H), 7.41 (s, 2H), 7.24 (s, 1H), 3.95 (s, 3H), 1.31 (s, 18H). $^{13}$C NMR (75 MHz, DMSO) δ 180.24, 152.28, 142.24, 140.82, 138.71, 127.15, 126.95, 126.32, 120.49, 119.33, 113.98, 112.88, 112.17, 112.05, 111.47, 104.92, 35.19, 34.03, 31.57.

ZL0775

(E)-N-(4-chloro-3-(trifluoromethyl)phenyl)-2-(5-cyano-1-methyl-1H-indol-3-yl)-2-oxoacetohydrazonoyl Cyanide (ZL0775)

Light brown solid (53 mg, 50%). $^1$H NMR (300 MHz, DMSO) δ 12.29 (s, 1H), 8.54 (d, J=11.2 Hz, 2H), 7.90 (s, 1H), 7.83-7.60 (m, 4H), 3.95 (s, 3H). $^{13}$C NMR (75 MHz, DMSO) δ 179.60, 141.94, 141.35, 138.77, 133.20, 126.98, 126.78, 126.44, 125.47, 121.53, 120.37, 116.45, 115.98, 112.87, 111.76, 111.49, 105.08, 34.01.

3-(1-Benzoyl-1H-indol-3-yl)-3-oxopropanenitrile (PW0179)

ZL0743 (184 mg, 1 mmol) and DAMP (12 mg, 0.1 mmol) were dissolved in dry DCM (5 mL), and the mixture solution was cooled to 0° C. with ice bath. Then NEt$_3$ (0.2 mL, 1.5 mmol) and benzoyl chloride (140 mg, 1 mmol) were added to the solution. The mixture solution was stirred at room temperature overnight. The mixture was extracted by DCM. The organic layer was then washed by saturated NaHCO$_3$ and brine. After dried over anhydrous Na$_2$SO$_4$, the residue was purified by silica gel column (PE/EA=10:1) to give PW0179 (153 mg, 51%) as a white solid. $^1$H NMR (300 MHz, Chloroform-d) δ 8.37-8.33 (m, 1H), 8.29-8.22 (m, 1H), 8.10 (s, 1H), 8.06-7.99 (m, 1H), 7.90-7.81 (m, 2H), 7.69-7.61 (m, 3H), 7.28 (s, 1H), 3.90 (s, 2H).

(E)-2-(1-Benzoyl-1H-indol-3-yl)-N-(4-chloro-3-(trifluoromethyl)phenyl)-2-oxoacetohydrazonoyl Cyanide (PW0175)

To a solution of 4-chloro-3-(trifluoromethyl)aniline (49 mg, 0.25 mmol) in 1 mL H$_2$O and 1 mL CH$_3$CN, 10% HCl (0.92 mmol) was added at 0° C. After stirring at rt for 30 min, NaNO$_2$ (21 mg, 0.3 mmol) in 1 mL H$_2$O was added. After stirring at 0° C. for 5 min, NaOAc (123 mg, 1.5 mmol) and PW0179 (72 mg, 0.25 mmol) in 2 mL EtOH/DMF (1:1) were added. The mixture was filtered to give the desired product (78 mg, 63%) as a yellow solid. $^1$H NMR (300 MHz, DMSO-d$_6$) δ 12.34 (s, 1H), 8.44-8.19 (m, 3H), 7.88 (dd, J=9.9, 5.1 Hz, 3H), 7.63 (t, J=7.5 Hz, 1H), 7.57-7.37 (m, 5H), 7.30 (dd, J=8.9, 2.5 Hz, 1H).

(E)-2-(1-Benzoyl-1H-indol-3-yl)-N-(3,5-di-tert-butylphenyl)-2-oxoacetohydrazonoyl Cyanide Light yellow solid (67 mg, 53%). $^1$H NMR (300 MHz, DMSO-d$_6$) δ 12.20 (s, 1H), 8.33 (s, 1H), 8.20 (dd, J=6.1, 3.1 Hz, 1H), 8.01 (dd, J=6.2, 3.2 Hz, 1H), 7.84-7.73 (m, 2H), 7.62 (d, J=7.5 Hz, 1H), 7.51-7.36 (m, 4H), 7.22 (dd, J=9.1, 1.6 Hz, 3H), 1.20 (s, 18H).

REFERENCES

A number of patents and publications are cited above in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

We claim:

1. A compound of Formula I or a pharmaceutically acceptable salt thereof, wherein:

Formula I

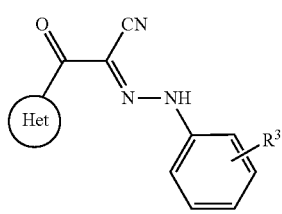

is a substituted or unsubstituted indole of the following structure (Formula Ia):

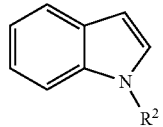

Formula Ia wherein said structure of Formula Ia is attached to the —(C=O)— group of Formula I via the 2-, 3-, 4-, 5-, 6-, or 7-position ring carbon atom;
wherein said ring is attached to the —(C=O)— group of Formula I at any available site;
$R^2$ is chosen from H, $COR^4$, $SO_2R^4$, —(O=C)$OR^4$, —(O=C)$NHR^4$, $C_1$-$C_6$ alkyl, —$CH_2Ph$, and $C_1$-$C_6$ alkylamine;
$R^3$ is substituted or unsubstituted group chosen from aryl, heteroaryl, cycloalkyl, β-lactam, γ-lactam, δ-lactam, ε-lactam, and heterocycle; wherein each group is fused with the phenyl ring;
$R^4$ is chosen from H, $C_1$-$C_6$ alkyl, $C_1$-$C_7$ cycloalkyl, aryl, and heteroaryl.

2. The compound of claim 1, wherein $R^2$ is H or a $C_1$-$C_6$ alkyl group.

3. The compound of claim 2, wherein said structure of Formula Ia is attached to the —(C=O)— group of Formula I via the 3-position ring carbon atom and wherein $R^2$ is methyl.

4. The compound of claim 1, wherein said Formula Ia group is bonded to the —(C=O)— group of Formula I via the 3-position ring carbon of Formula Ia.

5. The compound of claim 2, wherein $R^2$ is methyl.

6. The compound of claim 1, wherein $R^3$ is δ-lactam, wherein the 5, 6-ring carbons of the lactam ring are fused with the phenyl group of Formula I.

7. The compound of formula:

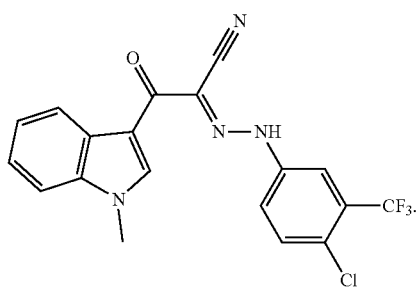

ZL0568

8. The compound of claim 6, wherein the compound is:

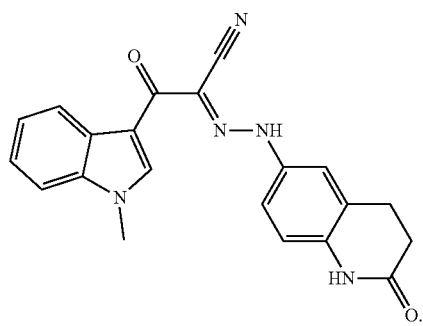

ZL06100

9. A method of activating latent HIV comprising contacting one or more cells with one or more compounds of claim 1.

10. A method of activating latent HIV comprising contacting one or more cells with ZL0568 and/or ZL06100

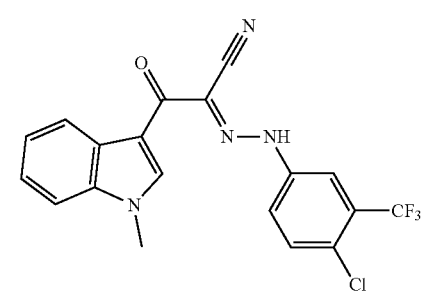

ZL0568

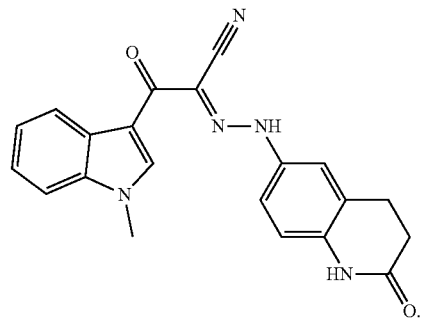

ZL06100

* * * * *